United States Patent
Ebrahimi Warkiani et al.

(10) Patent No.: US 10,806,845 B2
(45) Date of Patent: Oct. 20, 2020

(54) SYSTEM AND METHOD FOR INERTIAL FOCUSING MICROFILTRATION FOR INTRA-OPERATIVE BLOOD SALVAGE AUTOTRANSFUSION

(71) Applicants: Massachusetts Institute of Technology, Cambridge, MA (US); National University of Singapore, Singapore (SG)

(72) Inventors: Majid Ebrahimi Warkiani, Singapore (SG); Guofeng Guan, Singapore (SG); Kah Ping Andy Tay, Singapore (SG); Lidan Wu, Cambridge, MA (US); Jongyoon Han, Cambridge, MA (US); Chwee Teck Lim, Singapore (SG)

(73) Assignees: Massachusetts Institute of Technology, Cambridge, MA (US); National University of Singapore, Singapore (SG)

( * ) Notice: Subject to any disclaimer, the term of this patent is extended or adjusted under 35 U.S.C. 154(b) by 459 days.

(21) Appl. No.: 15/511,499

(22) PCT Filed: Sep. 17, 2015

(86) PCT No.: PCT/US2015/050628
§ 371 (c)(1),
(2) Date: Mar. 15, 2017

(87) PCT Pub. No.: WO2016/044555
PCT Pub. Date: Mar. 24, 2016

(65) Prior Publication Data
US 2017/0296732 A1    Oct. 19, 2017

Related U.S. Application Data

(60) Provisional application No. 62/051,581, filed on Sep. 17, 2014.

(51) Int. Cl.
*A61M 1/36* (2006.01)
*A61M 1/02* (2006.01)

(52) U.S. Cl.
CPC ............ *A61M 1/36* (2013.01); *A61M 1/0281* (2013.01); *A61M 2202/09* (2013.01);
(Continued)

(58) Field of Classification Search
CPC .. A61M 1/0281; A61M 1/36; A61M 2202/09; A61M 2202/20;
(Continued)

(56) References Cited

U.S. PATENT DOCUMENTS 5,842,996 A * 12/1998 Gruenfeld .......... A61B 5/02233
600/490
5,860,932 A *  1/1999 Goto .................. A61B 5/02116
600/485

(Continued)

FOREIGN PATENT DOCUMENTS

JP          2007-268490        10/2007
WO     WO 2007/021409 A1      2/2007

(Continued)

OTHER PUBLICATIONS

Sathyakumar S. Kuntaegowdanahalli, Ali Asgar S. Bhagat, Girish Kumar, and Ian Papautsky. Inertial microfluidics for continuous particle separation in spiral microchannels. Lap Chip 9:2973-2980 (2009). (Year: 2009).*

(Continued)

*Primary Examiner* — Leslie R Deak
(74) *Attorney, Agent, or Firm* — Hamilton, Brook, Smith & Reynolds, P.C.

(57) ABSTRACT

A system for intra-operative blood salvage autotransfusion is provided. The system comprises at least one inlet configured to receive whole blood of a patient; at least one curvilinear (Continued)

microchannel in fluid flow connection with the at least one inlet, the at least one curvilinear microchannel being adapted to isolate circulating tumor cells in the whole blood, based on cell size, along at least one portion of a cross-section of the at least one curvilinear microchannel; and at least two outlets in fluid flow connection with the at least one curvilinear microchannel, at least one outlet of the at least two outlets being configured to flow the circulating tumor cells isolated from the whole blood, and at least one other outlet of the at least two outlets being configured to flow at least a portion of a remainder of the whole blood, cleansed of the isolated circulating tumor cells, for return to the patient.

21 Claims, 7 Drawing Sheets (52) U.S. Cl.
CPC . *A61M 2202/20* (2013.01); *A61M 2205/0244* (2013.01); *A61M 2206/10* (2013.01)

(58) Field of Classification Search
CPC ...... A61M 2205/0244; A61M 2206/10; A61M 1/382; B01D 3/502753
See application file for complete search history.

(56) References Cited

U.S. PATENT DOCUMENTS

| | | | |
|---|---|---|---|
| 7,118,746 | B1 | 10/2006 | Naughton et al. |
| 7,294,503 | B2 | 11/2007 | Quake et al. |
| 7,309,486 | B1 | 12/2007 | Zamoyski |
| 7,374,937 | B1 | 5/2008 | Prockop et al. |
| 7,517,453 | B2 | 4/2009 | Bitensky et al. |
| 8,186,913 | B2 | 5/2012 | Toner et al. |
| 8,208,138 | B2 | 6/2012 | Papautsky et al. |
| 8,747,328 | B2 * | 6/2014 | Tichauer ............... A61B 5/0225 600/485 |
| 8,974,491 | B2 * | 3/2015 | Leschinsky ........ A61B 5/02225 606/202 |
| 9,458,489 | B2 | 10/2016 | Lim et al. |
| 9,789,485 | B2 | 10/2017 | Han et al. |
| 10,047,344 | B2 | 8/2018 | Poon et al. |
| 2007/0026381 | A1 | 2/2007 | Huang et al. |
| 2007/0131622 | A1 | 6/2007 | Oakey et al. |
| 2007/0263477 | A1 | 11/2007 | Sudarsan |
| 2007/0264675 | A1 | 11/2007 | Toner et al. |
| 2008/0128331 | A1 | 6/2008 | Lean et al. |
| 2009/0014360 | A1 | 1/2009 | Toner et al. |
| 2009/0050538 | A1 | 2/2009 | Lean et al. |
| 2009/0053749 | A1 | 2/2009 | Manalis et al. |
| 2009/0114607 | A1 | 5/2009 | Lean et al. |
| 2009/0136982 | A1 | 5/2009 | Tang et al. |
| 2009/0283452 | A1 | 11/2009 | Lean et al. |
| 2010/0150880 | A1 | 6/2010 | Aubin et al. |
| 2010/0314323 | A1 | 12/2010 | Lean et al. |
| 2010/0314327 | A1 | 12/2010 | Lean et al. |
| 2012/0028272 | A1 | 2/2012 | Sethu |
| 2013/0011210 | A1 | 1/2013 | Toner et al. |
| 2013/0109011 | A1 | 5/2013 | Park et al. |
| 2013/0130226 | A1 | 5/2013 | Lim et al. |
| 2014/0093867 | A1 | 4/2014 | Burke et al. |
| 2014/0093952 | A1 | 4/2014 | Serway |
| 2014/0154795 | A1 | 6/2014 | Lipkens et al. |
| 2015/0238963 | A1 | 8/2015 | Han et al. |
| 2017/0009208 | A1 | 1/2017 | Poon et al. |

FOREIGN PATENT DOCUMENTS

| | | |
|---|---|---|
| WO | WO 2007/081902 A3 | 7/2007 |
| WO | WO 2008/130977 A2 | 10/2008 |
| WO | WO 2010/115025 A2 | 10/2010 |
| WO | WO 2011/109762 A1 | 9/2011 |
| WO | WO 2013/050445 A1 | 4/2013 |
| WO | WO 2013/116696 A1 | 8/2013 |
| WO | WO 2014/046621 A1 | 3/2014 |
| WO | WO 2015/057159 | 4/2015 |
| WO | WO 2015/126528 A1 | 8/2015 |
| WO | WO 2016/044537 | 3/2016 |
| WO | WO 2016/044555 | 3/2016 |

OTHER PUBLICATIONS

Adams, A. A., et al., "Highly Efficient Circulating Tumor Cell Isolation from Whole Blood and Label-Free Enumeration Using Polymer-Based Microfluidics with an Integrated Conductivity Sensor," Journal of the American Chemical Society, 130(27): 8633-8641 (2008).
Allard, W.J., et al., "Tumor Cells Circulate in the Peripheral Blood of All Major Carcinomas but not in Healthy Subjects or Patients With Nonmalignant Diseases", Clin. Cancer Res., 10: 6897-6904 (Oct. 15, 2004).
Al-Nbaheen, M., et al., "Human Stromal (Mesenchymal) Stem Cells from Bone Marrow, Adipose Tissue and Skin Exhibit Differences in Molecular Phenotype and Differentiation Potential," Stem Cell Rev 9, 32-43 (2013).
Al-Soud, W.A. et al., "Purification and Characterization of PCR-Inhibitory Components in Blood Cells", Journal of Clinical Microbiology, 39(2): p. 485-493 (2001).
Antia, M., et al., "Microfluidic Approaches to Malaria Pathogenesis," Cellular Microbiology, 10(10): 1968-1974 (2008).
Arai, F., et al., "Tie2/Angiopoietin-1 Signaling Regulates Hematopoietic Stem Cell Quiescence in the Bone Marrow Niche," Cell 118, 149-161 (2004).
Arpornmaeklong, P., "Phenotypic Characterization, Osteoblastic Differentiation, and Bone Regeneration Capacity of Human Embryonic Stem Cell-Derived Mesenchymal Stem Cells", Stem Cells and Development, 18(7): 955-968 (2009).
Asmolov, E.S., "The Inertial Lift on a Spherical particle in a Plane Poiseuille Flow at Large Channel Reynolds Number," Journal of Fluid Mechanics, 381: 63-87 (1999).
Atkin, S.L., et al., "Hypotonic Lysis of Red Blood Cell Contamination from Human Anterior Pituitary Adenoma Cell Preparations", In Vitro Cell Dev Biol Anim, 31(9): p. 657-658 (Oct. 1995).
Awaya, N., et al., "Failure of Adult Marrow-Derived Stem Cells to Generate Marrow Stroma After Successful Hematopoietic Stem Cell Transplantation," Experimental Hematology 30, 937-942 (2002).
Ball, L.M., et al., "Cotransplantation of ex vivo Expanded Mesenchymal Stem Cells Accelerates Lymphocyte Recovery and May Reduce the Risk of Graft Failure in Haploidentical Hematopoietic Stem-Cell Transplantation," Blood 110, 2764-2767 (2007).
Ball, L.M., et al., "Graft Dysfunction and Delayed Immune Reconstitution Following Haploidentical Peripheral Blood Hematopoietic Stem Cell Transplantation," Bone Marrow Transplantation 35 Suppl 1, S35-38 (2005).
Battiwalla, M. & Hematti, P., "Mesenchymal Stem Cells in Hematopoietic Stem Cell Transplantation," Cytotherapy 11, 503-515 (2009).
Bhagat, "Inertial Microfluidics for Particle Separation and Filteration", Ph.D. thesis, College of Engineering, University of Cincinnati, 2009.
Bhagat A.A.S., et al., "Enhancing Particle Dispersion in a Passive Planar Micromixer Using Rectangular Obstacles," Journal of Micromechanics and Microengineering. 18(8): 085005 (9 pp) (2008).
Bhagat AAS, et al. "Inertial Microfluids for Sheath-Less High-Throughput Flow Cytometry", Biomedical Microdevices, 12(2): 187-95 (2010).
Bhagat, A.A.S., et al., "Inertial Microfluidics for Continuous Particle Filtration and Extraction", Microfluid Nanofluid 7: 217-226 (2009).
Bhagat, A.A.S., et al., "Pinched Flow Coupled Shear-Modulated Inertial Microfluidics for High-Throughput Rare Blood Cell Separation", The Royal Society of Chemistry Lab on a Chip, 11: 1870-1878 (2011).

(56) References Cited

OTHER PUBLICATIONS

Bhagat, A.A.S., et al., "Enhanced Particle Filtration in Straight Microchannels Using Shear-Modulated Inertial Migration," Physics of Fluids, 20: 101702 (4 pp) (2008).
Bhagat, A.A.S., et al., "Microfluidics for Cell Separation," Medical and Biological Engineering and Computing, 48: 999-1014 (2010).
Bianco, P., et al., "Bone Marrow Stromal Stem Cells: Nature, Biology, and Potential Applications," Stem Cells 19, 180-192 (2001).
Born, C., et al., "Estimation of Disruption of Animal Cells by Laminar Shear Stress," Biotechnology and Bioengineering, 40(9): p. 1004-1010 (1992).
Boxall, S.A. & Jones, E., "Markers for Characterization of Bone Marrow Multipotential Stromal Cells," Stem Cells Int 2012, 975871 (2012).
Bruil, A., et al., "Asymmetric Membrane Filters for the Removal of Leukocytes from Blood", Journal of Biomedical Materials Research, 25(12): 1459-1480 (1991).
Calvi, L.M., et al., "Osteoblastic Cells Regulate the Haematopoietic Stem Cell Niche," Nature 425, 841-846 (2003).
Cao, X., et al., "Irradiation Induces Bone Injury by Damaging Bone Marrow Microenvironment for Stem Cells," Proceedings of the National Academy of Sciences of the United States of America 108, 1609-1614 (2011).
Chatterjee, A., et al., "Inertial Microfluidics for Continuous Separation of Cells and Particles", Proceedings of the SPIE, vol. 7929: 10 pgs. (2011).
Chen, F.M., et al., "Toward Delivery of Multiple Growth Factors in Tissue Engineering," . . . Biomaterials 31, 6279-6308 (2010).
Chen, L.W., et al., "Analysis of Allogenicity of Mesenchymal Stem Cells in Engraftment and Wound Healing in Mice," Plos One 4(2009).
Chin, C.D., et al., "Lab-On-A-Chip Devices for Global Health: Past Studies and Future Opportunities," Lab-on-a-Chip,7:41-57 (2007).
Choi, S., et al., "Microfluidic Self-Sorting of Mammalian Cells to Achieve Cell Cycle Synchrony by Hydrophoresis," Analytical chemistry,.81(5): 1964-1968 (2009).
Christopeit, M., et al., Marked Improvement of Severe Progressive Systemic Sclerosis after Transplantation of Mesenchymal Stem Cells from an Allogeneic Haploidentical-Related Donor Mediated by Ligation of CD137L. Leukemia 22, 1062-1064 (2008).
Chun, B. et al., "Inertial Migration of Neutrally Buoyant Particles in a Square Duct: An Investigation of Multiple Equilibrium Positions", Physics of Fluids, 18(3): p. 031704 (2006).
Clines, G.A., "Prospects for osteoprogenitor stem cells in fracture repair and osteoporosis", Current Opinion in Organ Transplantation, (2010), 15:(1): 73-78.
Cooke, B.M., et al., "Falciparum Malaria: Sticking Up, Standing Out, and Out-Standing," Parasitology Today. 16(10): 416-420 (2000).
Cooper, S., "Rethinking Synchronization of Mammalian Cells for Cell Cycle Analysis," Cellular and Molecular Life Sciences, 60(6): 1099-1106 (2003).
Coupier, G., et al., "Noninertial Lateral Migration of Vesicles in Bounded Poiseuille Flow," Physics of Fluids. 20(11): 4 (2008).
Cranston, H.A., et al. "Plasmodium Falciparum Maturation Abolishes Physiologic Red Cell Deformability," Science. 223(4634): 400-403 (1984).
Cristofanilli, M., et a., "Circulating Tumor Cells, Disease Progression, and Survival in Metastatic Breast Cancer", N. Engl. J. Med., 351(8), 781-791 (Aug. 19, 2004).
Dean, W.R., LXXII. The Stream-Line Motion of Fluid in a Curved Pipe (Second Paper), The London, Edinburgh and Dublin Philosophical Magazine and Journal of Science, Series 7, 5:30, 673-695 (1928).
Dean, W.R., XVI. Note on the Motion of Fluid in a Curved Pipe, The London, Edinburgh and Dublin Philosophical Magazine and Journal of Science, Series 7, 4(20): p. 208-223 (1927).
Delamarche, E., et al., "Stability of Molded Polydimethylsiloxane Microstructures," Advanced Materials, 9(9): 741-746 (1997).

Demirev, P.A., et al. "Detection of Malaria Parasites in Blood by Laser Desorption Mass Spectrometry," Analytical Chemistry. 74(14): 3262-3266 (2002).
Di Carlo D. "Inertial Microfluidics", The Royal Society of Chemistry Lab on a chip, 9(21):3038-46 (2009).
Di Carlo, D., et al., "Continuous Inertial Focusing, Ordering, and Separation of Particles in Microchannels", Proceedings of the National Academy of Sciences, 104(48): p. 18892-18897.
DiCarlo, D., et al., "Equilibrium Separation and Filtration of Particles Using Differential Inertial Focusing", Anal. Chem., 80(6): p. 2204-2211 (2008).
Ding, L. & Morrison, S.J., "Haematopoietic Stem Cells and Early Lymphoid Progenitors Occupy Distinct Bone Marrow Niches," Nature 495, 231-235 (2013).
Docheva, D., et al., "Researching into the cellular shape, volume and elasticity of mesenchymal stem cells, osteoblasts and osteosarcoma cells by atomic force microscopy", J. Cell. Mol. Med., 12(2): 537-552 (2008).
Dominici, et al., Cytotherapy 8(4): 315-317 (2006).
Dondorp, A.M., et al., "Abnormal Blood Flow and Red Blood Cell Deformability in Severe Malaria," Parasitology Today. 16(6): 228-232 (2000).
Downey, G .P., et al., "Retention of Leukocytes in Capillaries: Role of Cell Size and Deformability," Journal of Applied Physiology, 69(5): 1767-1778 (1990).
Ehninger, A. & Trumpp, A. The Bone Marrow Stem Cell Niche Grows Up: Mesenchymal Stem Cells and Macrophages Move In, J Exp Med 208, 421-428 (2011).
El-Badri, N.S., et al., "Osteoblasts Promote Engraftment of Allogeneic Hematopoietic Stem Cells," Experimental Hematology 26, 110-116 (1998).
Evans, E., et al., "Static and Dynamic Rigidities of Normal and Sickle Erythrocytes," Journal of Clinical Investigation, 73(2):477-488 (1984).
Fan, R, et al., "Integrated Barcode Chips for Rapid, Multiplexed Analysis of Proteins in Microliter Quantities of Blood," Nature Biotechnology. 26(12): 1373-1378 (2008).
Fiebig, E, et al., "Rapid Leukocyte Accumulation by "Spontaneous" Rolling and Adhesion in the Exteriorized Rabbit Mesentery," International Journal of Microcirculation Clinical and Experimental. 10(2): 127-144 (1991).
Fouillard, L., et al., "Infusion of Allogeneic-Related HLA Mismatched Mesenchymal Stem Cells for the Treatment of Incomplete Engraftment Following Autologous Haematopoietic Stem Cell Transplantation," Leukemia 21, 568-570 (2007).
Fredriksson, K., et al., "Red Blood Cells Inhibit Proliferation and Stimulate Apoptosis in Human Lung Fibroblasts In Vitro, Scandinavian Journal of Immunology," 59(6): p. 559-565 (2004).
Fujiwara, H., et al., "Red Blood Cell Motions in High-Hematocrit Blood Flowing Through a Stenosed Microchannel," Journal of Biomechanics. 42(7): 838-843 (2009).
Gascoyne, P., et al. "Microsample Preparation by Dielectrophoresis: Isolation of Malaria," Lab on a Chip 2(2): 70-75 (2002).
Gleghorn, J.P., et al., "Capture of Circulating Tumor Cells from Whole Blood of Prostate Cancer Patients Using Geometrically Enhanced Differential Immunocapture (GEDI) and a Prostate-Specific Antibody," Lab on a Chip, 10(1): 27-29 (2010).
Glenister, F.K., et al., "Contribution of Parasite Proteins to Altered Mechanical Properties of Malaria-Infected Red Blood Cells," Blood, 99(3):1060-1063 (2002).
Goldsmith, H.L., et al., "Margination of Leukocytes in Blood Flow Through Small Tubes," Microvascular Research. 27(2): 204-222 (1984).
Goldsmith, H.L., et al., "Robin Fåhraeus: Evolution of his Concepts in Cardiovascular Physiology," American Journal of Physiology. 257(3): H1005-H1015 (1989).
Gossett, D.R., et al., "Label-Free Cell Separation and Sorting in Microfluidic Systems," Anal. Bioanal. Chem., 397:3249-3267 (2010).
Granero-Molto, F., et al., "Regenerative Effects of Transplanted Mesenchymal Stem Cells in Fracture Healing," Stem Cells 27, 1887-1898 (2009).

(56) References Cited

OTHER PUBLICATIONS

Greenbaum, A., et al., "CXCL12 in Early Mesenchymal Progenitors is Required for Haematopoietic Stem-Cell Maintenance," Nature 495, 227-230 (2013).

Guan, et al., "Spiral Microchannel with Rectangular and Trapezoidal Cross-Sections for Size Based Particle Separation", Scientific Reports, 3:1475 (2013), 9 pages.

Gupta, A, et al., "Effect of Aspect Ratio on Inertial Migration of Neutrally Buoyant Spheres in a Rectangular Channel," 47th AIAA Aerospace Sciences Meeting, Orlando, FL (Jan. 5-8, 2009).

Hampton, R.E., et al., "Migration of Particles Undergoing Pressure-Driven Flow in a Circular Conduit," Journal of Rheology, 41(3): 621 (1997).

Han, K and A.B. Frazier, "Lateral-Driven Continuous Dielectrophoretic Microseparators for Blood Cells Suspended in a Highly Conductive Medium", The Royal Society of Chemistry, Lab on a Chip, 8(7): 1079-1086 (2008).

Han, K.-H., et al., "Paramagnetic Capture Mode Magnetophoretic Microseparator for High Efficiency Blood Cell Separations", The Royal Society of Chemistry, 6(2): p. 265-273 (2006).

Heo, S.C., et al., Tumor Necrosis Factor-Alpha-Activated Human Adipose Tissue-Derived Mesenchymal Stem Cells Accelerate Cutaneous Wound Healing Through Paracrine Mechanisms. J Invest Dermatol 131, 1559-1567 (2011).

Herricks, T., et al., "Deformability Limits of Plasmodium Falciparum-Infected Red Blood Cells," Cellular Microbiology. 11(9): 1340-1353 (2009).

Ho, M., et al., "Visualization of Plasmodium Falciparum-Endothelium Interactions in Human Microvasculature: Mimicry of Leukocyte Recruitment," Journal of Experimental Medicine. 192(8): 1205-1211 (2000).

Hooper, A.T., et al., "Engraftment and Reconstitution of Hematopoiesis is Dependent on VEGFR2-Mediated Regeneration of Sinusoidal Endothelial Cells," Cell Stem Cell 4, 263-274 (2009).

Horwitz, E.M., "MSC: A Coming of Age in Regenerative Medicine," Cytotherapy 8, 194-195 (2006).

Horwitz, E.M., et al., "MSCs in Hematopoietic Cell Transplantation," Biol Blood Marrow Transplant 17, S21-29 (2011).

Hou, H.W., et al., "Microfluidic Devices for Blood Fractionation", Micromachines, 2(3): p. 319-343 (2011).

Hou, H.W., et al., "Deformability Based Cell Margination—A Simple Microfluidic Design for Malaria-Infected Erythrocyte Separation," Lab on a chip, 10(19): 2605-2613 (2010).

Hou, H.W., et al., "Deformability Study of Breast Cancer Cells Using Microfluidics," Biomedical Microdevices, 11(3): p. 557-564 (2009).

Huang, L.R., et al., "Continuous Particle Separation Through Deterministic Lateral Displacement", Science, 304: 987-990 (2004).

Hur, S.C., et al., "Deformability-Based Cell Classification and Enrichment Using Inertial Microfluidics", The Royal Society of Chemistry, Lab on a Chip, 11(5): 912-920 (2011).

Hutson, E.L., et al., "Rapid Isolation, Expansion, and Differentiation of Osteoprogenitors from Full-Term Umbilical Cord Blood", Tissue Engineering, 11(9-10): 1407-1420 (2005).

Inglis, D.W., et al. "Continuous Microfluidic Immunomagnetic Cell Separation", Applied Physics Letters, 85(21): 5093-5095 (2004).

Isolation of Monomuclear Cells from Human Cord Blood by Density Gradient Centrifugation, MACS Miltenyi Biotec (2008) 1 pg.

Itoh, S., "Bone Marrow-Derived HipOP Cell Population is Markedly Enriched in Osteoprogenitors", International Journal of Molecular Sciences, 13(8): 10229-10235 (2012).

Jaeger, BAS, et al., "Abstract P2-01-02: Circulating Tumor Cells (CTC) may Express HER2/neu in Patients With Early HER2/neu Nagative Breast Cancer—Results of the German SUCCESS C Trial", Cancer Research, 72(24 Suppl): Abstract nr P2-01-02 (2012).

Jäggi, R.D., et al., "Microfluidic Depletion of Red Blood Cells from Whole Blood in High-Aspect-Ratio Microchannels," Microfluidics and Nanofluidics. 3(1): 47-53 (2007).

Jain, A., et al., "Determinants of Leukocyte Margination in Rectangular Microchannels," PLoS One. 4(9):e7104 (8 pp) (2009).

Jung, S., et al., "Large-Scale Production of Human Mesenchymal Stem Cells for Clinical Applications," Biotechnology and Applied Biochemistry 59, 106-120 (2012).

Karl, S., et al., "Enhanced Detection of Gametocytes by Magnetic Deposition Microscopy predicts higher potential for Plasmodium Falciparum Transmission," Malaria Journal. 7(1): 66 (2008).

Keating, A., "Mesenchymal Stromal Cells: New Directions," Cell Stem Cell 10, 709-716 (2012).

Kim, U., et al., "Selection of Mammalian Cells Based on Their Cell-Cycle Phase Using Dielectrophoresis," Proceedings of the National Academy of Sciences, 104(52): 20708 (2007).

Kolf, C.M., et al., "Mesenchymal Stromal Cells—Biology of Adult Mesenchymal Stem Cells: Regulation of Niche, Self-Renewal and Differentiation," Arthritis Research & Therapy 9(2007).

Kong, Y., et al. "Association of an Impaired Bone Marrow Microenvironment with Secondary Poor Graft Function after Allogeneic Hematopoietic Stem Cell Transplantation," Biol Blood Marrow Transplant 19, 1465-1473 (2013).

Kopp, H.G., et al., "Functional Heterogeneity of the Bone Marrow Vascular Niche," Ann N Y Acad Sci 1176, 47-54 (2009).

Kuntaegowdanahalli, S.S., et al., "Inertial microfluidics for continuous particle separation in spiral microchannels", The Royal Society of Chemistry, Lab on a Chip, 9(20): 2973-2980 (2009).

Lange, C., et al., "Radiation Rescue: Mesenchymal Stromal Cells Protect from Lethal Irradiation," Plos One 6, e14486 (2011).

Lara, O., et al., "Enrichment of Rare Cancer Cells Through Depletion of Normal Cells Using Density and Flow-Through, Immunomagnetic Cell Separation," Experimental hematology, 32(10): 891-904 (2004).

Le Blanc, K., et al., "Transplantation of Mesenchymal Stem Cells to Enhance Engraftment of Hematopoietic Stem Cells," Leukemia 21, 1733-1738 (2007).

Lee, R.H., et al., "Characterization and Expression Analysis of Mesenchymal Stem Cells from Human Bone Marrow and Adipose Tissue," Cell Physiol Biochem 14, 311-324 (2004).

Lee, S.S.., et al., "Extensional Flow-Based Assessment of Red Blood Cell Deformability Using Hyperbolic Converging Microchannel," Biomedical Microdevices, (2009).

Lee, W. C., et al., "Multivariate Biophysical Markers Predictive of Mesenchymal Stromal Cell Multipotency", PNAS, E4409-E4418, (2014).

Lee, W.C., "High-throughput cell cycle synchronization using inertial forces in spiral microchannels", Lab Chip, 2011, 11: 1359-1367.

Li, Z., et al., "Epigenetic Dysregulation in Mesenchymal Stem Cell Aging and Spontaneous Differentiation," Plos One 6, e20526 (2011).

Lincoln, B., et al., "Deformability-Based Flow Cytometry," Cytometry Part A, 59(2): 203-209 (2004).

Loffredo, F.S., et al., "Bone Marrow-Derived Cell Therapy Stimulates Endogenous Cardiomyocyte Progenitors and Promotes Cardiac Repair," Cell Stem Cell 8, 389-398 (2011).

Marinkovic, M., et al., "Febrile Temperature Leads to Significant Stiffening of Plasmodium Falciparum Parasitized Erythrocytes," American Journal of Physiology—Cell Physiology. 296(1):C59-C64 (2009).

Matas, J.-P., et al., "Inertial Migration of Rigid Spherical Particles in Poiseuille Flow," Journal of Fluid Mechanics, 515: 171-195 (2004).

Matas, J.P., et al., "Lateral Forces on a Sphere," Oil & Gas Science and Technology, 59(1): 59-70 (2004).

McDonald, J.C., et al., "Poly(dimethylsiloxane) as a Material for Fabricating Microfluidic Devices," Accounts of Chemical Research. 35(7): 491-499 (2002).

Members of the Toxicogenonics Research Consortium, "Standardizing Global Gene Expression Analysis Between Laboratories and Across Platforms", Nature Methods, 2(5): p. 351-356 (May 2005).

Metzner, K., et al., "Abstract 3619: The Absence of Cleaved Caspase-3 in Circulating Tumor Cells Detected Using a Non-Enrichment Based Assay", Cancer Res., 72, Supplement 1 (2012).

Migita, S., et al., "Cell Cycle and Size Sorting of Mammalian Cells Using a Microfluidic Device," Analytical Methods, 2: 657-660 (2010).

(56) References Cited

OTHER PUBLICATIONS

Mohamed, H., et al., "Isolation of Tumor Cells Using Size and Deformation," Journal of Chromatography A, 1216(47): 8289-8295 (2009).
Morad, V., et al., "The Myelopoietic Supportive Capacity of Mesenchymal Stromal Cells is Uncoupled from Multipotency and is Influenced by Lineage Determination and Interference with Glycosylation," Stem Cells 26, 2275-2286 (2008).
Nagrath, S., et al., "Isolation of Rare Circulating Tumour Cells in Cancer Patients by Microchip Technology," Nature, 450(7173): 1235-1239 (2007).
Nash, G.B., et al., "Abnormalities in the Mechanical Properties of Red Blood Cells Caused by Plasmodium Falciparum," Blood. 74(2): 855-861 (1989).
Naveiras, O., et al., "Bone-Marrow Adipocytes as Negative Regulators of the Haematopoietic Microenvironment," Nature 460, 259-263 (2009).
Needham, P.L., "Separation of Human Blood Using 'Mono-Poly Resolving Medium'" Journal of Immunological Methods, 99: 283-284 (1986).
Neiva, K., et al., "The Role of Osteoblasts in Regulating Hematopoietic Stem Cell Activity and Tumor Metastasis," Braz J Med Biol Res 38, 1449-1454 (2005).
Nivedita and Papautsky, Biomicrofluidics, 7:054101-1-14 (2013).
Noort, W.A., et al., "Mesenchymal Stem Cells Promote Engraftment of Human Umbilical Cord Blood-Derived CD34(+) Cells in NOD/SCID Mice," Experimental Hematology 30, 870-878 (2002).
Notification Concerning Transmittal of International Preliminary Report on Patentability for International Application No. PCT/US2011/027276, entitled: "Microfluidics Sorter for Cell Detection and Isolation," Date of Issuance: Sep. 4, 2012, dated Sep. 13, 2012.
Notification Concerning Transmittal of International Preliminary Report on Patentability for International Application No. PCT/SG2013/000412, titled: "Micro-Fluidic Device and Uses Thereof," dated Nov. 25, 2013.
Notification Concerning Transmittal of International Preliminary Report on Patentability, with International Preliminary Report on Patentability, for International Application No. PCT/US2015/000029, entitled "Biophysically Sorted Osteoprogenitors From Culture Expanded Bone Marrow Derived Mesenchymal Stromal Cells (MSCs)", dated Sep. 1, 2016.
Notification of Transmittal of the International Search Report and the Written Opinion of the International Searching Authority for Int'l Application No. PCT/SG2013/000412, titled: "Micro-Fluidic Device and Uses Thereof,", dated Nov. 25, 2013.
Notification of Transmittal of the International Search Report and the Written Opinion of the International Searching Authority, or the Declaration, International Search Report and Written Opinion for International Application No. PCT/US2011/027276, entitled: "Microfluidics Sorter for Cell Detection and Isolation," (dated May 13, 2011).
Notification of Transmittal of the International Search Report and the Written Opinion of the International Searching Authority, with the International Search Report and the Written Opinion, for International Application No. PCT/US2015/000029, entitled "Biophysically Sorted Osteoprogenitors From Culture Expanded Bone Marrow Derived Mesenchymal Stromal Cells (MSCs)", dated Jun. 4, 2015.
Olbrich, M., et al., "Isolation of Osteoprogenitors from Human Jaw Periosteal Cells: a Comparison of Two Magnetic Separation Methods", Plos One, 7(10): e47176 (2012).
Ookawara, S., et al., "Quasi-Direct Numerical Simulation of Lift Force-Induced Particle Separation in a Curved Microchannel by Use of a Macroscopic Particle Model", Chemical Engineering Science, 62(9): 2454-2465 (2007).
Ookawara, S., et al., "Feasibility Study on Concentration of Slurry and Classification of Contained Particles by Microchannel", Chemical Engineering Journal, 101(1-3): 171-178 (2004).
Owen, T.A., et al., "Isolationand Culture of Rosent Osteoprogenitor Cells", Methods in Molecular Biology, 455, 3-18 (2008).

Panaro, N.J., et al., "Micropillar Array Chip for Integrated White Blood Cell Isolation and PCR", Biomolecular Engineering, 21(6): 157-162 (2005).
Park, D., et al., "Endogenous Bone Marrow MSCs are Dynamic, Fate-Restricted Participants in Bone Maintenance and Regeneration," Cell Stem Cell 10, 259-272 (2012).
Park, J.S., et al., "The Promotion of Chondrogenesis, Osteogenesis, and Adipogenesis of Human Mesenchymal Stem Cells by Multiple Growth Factors Incorporated into Nanosphere-Coated Microspheres," Biomaterials 32, 28-38 (2011).
Paterlini-Brechot, P. and Benali, N.L.,"Circulating Tumor Cells (CTC) Detection: Clinical Impact and Future Directions," Cancer letters, 253(2): p. 180-204 (2007).
Paulitschke, M., et al., "Membrane Rigidity of Red Blood Cells Parasitized by Different Strains of Plasmodium Falciparum," Journal of Laboratory and Clinical Medicine, 122(5): 581-589 (1993).
Phinney, D.G. & Prockop, D.J., "Concise Review: Mesenchymal Stem/Multipotent Stromal Cells: The State of Transdifferentiation and Modes of Tissue Repair—Current Views," Stem Cells 25, 2896-2902 (2007).
Poncin, G., et al., "Characterization of Spontaneous Bone Marrow Recovery After Sublethal Total Body Irradiation: Importance of the Osteoblastic/Adipocytic Balance," Plos One 7, e30818 (2012).
Poon, Z., et al., "Bone Marrow Regeneration Promoted by Biophysical Sorted Osteoprogenitors from Mesenchyman Stromal Cells", Stem Cells Translational Medicine, 4(1): 56-65 (2015).
Popel, A.S. et al., "Microcirculation and Hemorheology," Annual Review of Fluid Mechanics. 37: 43-69 (2005).
Powell, A.A., et al., "Single Cell Profiling of Circulating Tumor Cells: Transcriptional Heterogeneity and Diversity from Breast Cancer Cell Lines", PLOS One, 7(5): e33788, 11 pgs. (2012).
Price, A.K., et al., "Monitoring Erythrocytes in a Microchip Channel that Narrows Uniformly: Towards an Improved Microfluidic-Based Mimic of the Microcirculation," Journal of Chromatography A, 1111(2): 220-227 (2006).
Pries, A.R., et al., "Biophysical Aspects of Blood Flow in the Microvasculature," Cardiovascular Research. 32(4): 654-667 (1996).
Raaijmakers, M.H., et al., "Bone Progenitor Dysfunction Induces Myelodysplasia and Secondary Leukaemia," Nature 464, 852-857 (2010).
Ranganath, S.H., et al., "Harnessing the Mesenchymal Stem Cell Secretome for the Treatment of Cardiovascular Disease," Cell Stem Cell 10, 244-258 (2012).
Riethdorf, S., et al., "Detection of Circulating Tumor Cells in Peripheral Blood of Patients with Metastatic Breast Cancer: A Validation Study of the CellSearch System", Clin. Cancer Res., 13(3): 920-928 (2007).
Ring, A., et al. "Circulating Tumour Cells in Breast Cancer", The lanced Oncology, 5: 79-88 (2004).
Robey, P.G. & Termine, J.D., "Human Bone Cells in vitro," Calcif Tissue Int 37, 453-460 (1985).
Rosenbluth, M.J., et al., "Force Microscopy of Nonadherent Cells: A Comparison of Leukemia Cell Deformability," Biophysical Journal, 90(8): 2994-3003 (2006).
Russom, A., et al., "Differential Inertial Focusing of Particles in Curved Low-Aspect-Ratio Microchannels," New Journal of Physics, 11: 075025 (9 pp) (2009).
Sacchetti, B., et al., "Self-Renewing Osteoprogenitors in Bone Marrow Sinusoids can Organize a Hematopoietic Microenvironment", Cell, 131(2): 324-336 (2007).
Safeukui, I., et al., "Retention of Plasmodium Falciparum Ring-Infected Erythrocytes in the Slow, Open Microcirculation of the Human Spleen," Blood. 112(6):2520-2528 (2008).
Schaff, U.Y., et al., "Vascular Mimetics Based on Microfluidics for Imaging the Leukocyte-Endothelial Inflammatory Response," Lab-on-a-Chip, 7:448-456 (2007).
Schallmoser, K., et al. "Rapid Large-Scale Expansion of Functional Mesenchymal Stem Cells from Unmanipulated Bone Marrow Without Animal Serum," Tissue Engineering Part C—Methods 14, 185-196 (2008).
Schmid-Schonbein, G.W., et al., "Morphometry of Human Leukocytes," Blood, 56(5): 866-875 (1980).

(56) References Cited

OTHER PUBLICATIONS

Segre, G. et al., "Behaviour of Macroscopic Rigid Spheres in Poiseuille Flow," J. Fluid Mech, 14: 115-136 (1962).
Segre, G. et al., "Radial Particle Displacements in Poiseuille Flow of Suspensions," Nature, 189: 209-210 (1961).
Selzner, N ., et al., "Water induces autocrine stimulation of tumor cell killing through ATP release and P2 receptor binding", Cell Death and Differentiation, 11: p. S 172-S 180 (2004).
Seo, J., et al., Membrane-Free microfiltration by asymmetric inertial migration, Applied Physics Letters, 91(3): p. 033901-3 (2007).
Sethu, P., et al., "Microfluidic Isolation of Leukocytes from Whole Blood for Phenotype and Gene Expression Analysis", Analytical Chemistry, 78(15): 5453-5461 (2006).
Sethu, P., et al., "Microfluidic Diffusive Filter for Apheresis (Leukapheresis)," Lab on a Chip, 6(1): p. 83-89 (2006).
Shelby, J.P., et al., "A Microfluidic Model for Single-Cell Capillary Obstruction by Plasmodium Falciparum-Infected Erythrocytes," Proceedings of the National Academy of Sciences of the United States of America, 100(25): 14618-14622 (2003).
Shevkoplyas, S.S., et al., "Biomimetic Autoseparation of Leukocytes from Whole Blood in a Microfluidic Device," Analytical Chemistry. 77(3): 933-937 (2005).
Shevkoplyas, S.S., et al., "Direct Measurement of the Impact of Impaired Erythrocyte Deformability on Microvascular Network Perfusion in a Microfluidic Device," Lab on a Chip. 6(7): 914-920 (2006).
Shim, I.H., et al, "Alkaline Phosphatase Activity as a redictive Marker of Osteogenesis in Human Bone Marrow-Derived Mesenchymal Stem Cells But Not Umbilical Cord Blood-Derived Mesenchymal Stem Cells", *53rd Annual Meeting of the Orthopaedic Research Society*, Feb. 1, 2007, XP055383771, Poster No. 0465.
Shirota, T. & Tavassoli, M. Cyclophosphamide-induced alterations of bone marrow endothelium: implications in homing of marrow cells after transplantation. Experimental Hematology 19, 369-373 (1991).
Stevens, D.Y., et al., "Enabling a Microfluidic Immunoassay for the Developing World by Integration of On-Card Dry Reagent Storage," Lab on a Chip. 8(12): 2038-2045 (2008).
Subramanian, M.R., et al., "Bone Morphogenetic Proteins: Periodontal Regeneration", N. Am. J. Med. Sci. Mar. 2013, 5(3): 161-168.
Suresh, S., et al., "Connections Between Single-Cell Biomechanics and Human Disease States: Gastrointestinal Cancer and Malaria," Acta Biomaterialia, 1(1): 15-30 (2005).
Sutton, N., et al., "A Novel Instrument for Studying the Flow Behaviour of Erythrocytes Through Microchannels Simulating Human Blood Capillaries," Microvascular Research, 53(3): 272-281 (1997).
Taichman, R.S., et al., "Human Osteoblasts Support Human Hematopoietic Progenitor Cells in vitro Bone Marrow Cultures," Blood 87, 518-524 (1996).
Tan, S.J., et al., "Microdevice for the Isolation and Enumeration of Cancer Cells from Blood," Biomedical Microdevices, 11(4): 883-892 (2009).
Thevoz, P., et al., "Acoustophoretic Synchronization of Mammalian Cells in Microchannels," Analytical chemistry 82: 3094-3098 (2010).
Toner, M. and Irimia, D., "Blood-on-a-Chip," Annual Review of Biomedical Engineering, 7:77-103 (2005).
Vona, G., et al., "Enrichment, Immunomorphological, and Genetic Characterization of Fetal Cells Circulating in Maternal Blood," American Journal of Pathology, 160(1): 51-58 (2002).
Wang, X., et al., "Progenitors systemically transplanted into neonatal mice localize to areas of active bone formation in vivo: implications of cell therapy for skeletal diseases", Stem Cells, 24(8): 1869-1878 (2006).
Wersto, R.P., et al., "Doublet Discrimination in DNA Cell-Cycle Analysis," Cytometry Part B: Clinical Cytometry, 46(5): 296-306 (2001).
Whitfield, M.J., et al., "Onset of heterogeneity in culture-expanded bone marrow stromal cells", Stem Cell Research, 11: 1365-1377 (2013).

Whitfield, M.L., et al., "Identification of Genes Periodically Expressed in the Human Cell Cycle and Their Expression in Tumors," Molecular Biology of the Cell, 2002. 13(6): 1977-2000 (2002).
Xia, Y. et al., "Soft Lithography," Annual Review of Materials Science, 28(1): 153-184 (1998).
Tong, X, et al., "Separation and Characterization of Red Blood Cells with Different Membrane Deformability Using Steric Field-flow Fractionation," Journal of Chromatography B: Biomedical Sciences and Applications. 674(1): 39-47 (1995).
Yamada, M. et al., "Hydrodynamic filtration for on-chip particle concentration and classification utilizing microfluidics", The Royal Society of Chemistry, Lab on a Chip, 5(11): 1233-1239 (2005).
Yamada, M., et al., "Pinched Flow Fractionation: Continuous Size Separation of Particles Utilizing a Laminar Flow Profile in a Pinched Microchannel," Anal. Chem., 76(18): 5465-5471 (2004).
Yang, X., et al., "Marrow Stromal Cell Infusion Rescues Hematopoiesis in Lethally Irradiated Mice despite Rapid Clearance after Infusion," Adv Hematol 2012, 142530 (2012).
Yeh, C., et al., "Transient Lateral Transport of Platelet-Sized Particles in Flowing Blood Suspensions," Biophysical Journal, 66(5): 1706-1716 (1994).
Zabaglo, L., et al., "Cell Filtration—Laser Scanning Cytometry for the Characterisation of Circulating Breast Cancer Cells," Cytometry Part A, 55(2): 102-108 (2003).
Zeng, L., et al., "Wall-Induced Forces on a Rigid Sphere at Finite Reynolds Number," Journal of Fluid Mechanics, 536: 1-25 (2005).
Zeng, L., et al., Endothelial Injury, an Intriguing Effect of Methotrexate and Cyclophosphamide During Hematopoietic Stem Cell Transplantation in Mice. Transplant Proc 40, 2670-2673 (2008).
Zhao, R., et al., "Micro-Flow Visualization of Red Blood Cell-Enhanced Platelet Concentration at Sudden Expansion," Annals of Biomedical Engineering. 36(7): 1130-1141 (2008).
Zheng, S., et al., "Membrane Microfilter Device for Selective Capture, Electrolysis and Genomic Analysis of Human Circulating Tumor Cells," Journal of Chromatography A, 1162(2): 154-161 (2007).
Zheng, S., et al., "Streamline-Based Microfluidic Device for Erythrocytes and Leukocytes Separation," Journal of Microelectromechanical Systems, 17(4): 1029-1038 (2008).
Zimmerman, P.A., et al., "Diagnosis of Malaria by Magnetic Deposition Microscopy," American Journal of Tropical Medicine and Hygiene. 74(4): 568-572 (2006).
Non-Final Office Action dated Mar. 26, 2014 for U.S. Appl. No. 13/582,263, "Microfluidics Sorter for Cell Detection and Isolation".
Final Office Action dated Dec. 5, 2014 for U.S. Appl. No. 13/582,263, "Microfluidics Sorter for Cell Detection and Isolation".
Non-Final Office Action dated Apr. 22, 2015 for U.S. Appl. No. 13/582,263, "Microfluidics Sorter for Cell Detection and Isolation".
Final Office Action dated Oct. 16, 2015 for U.S. Appl. No. 13/582,263, "Microfluidics Sorter for Cell Detection and Isolation".
Non-Final Office Action dated Aug. 5, 2016 for U.S. Appl. No. 14/429,280, "Micro-Fluidic Device and Uses Thereof".
Final Office Action dated Jan. 19, 2017 for U.S. Appl. No. 14/429,280, "Micro-Fluidic Device and Uses Thereof".
Office Action dated May 5, 2017 for U.S. Appl. No. 14/429,280, "Micro-Fluidic Device and Uses Thereof".
Notice of Allowance and Fees Due for U.S. Appl. No. 13/582,263, "Microfluidics Sorter for Cell Detection and Isolation", dated May 20, 2016.
International Preliminary Report on Patentability and the Written Opinion of the International Searching Authority for International Application No. PCT/US2015/050604, entitled: "Microfluidic System and Method for Perfusion Bioreactor Cell Retention" dated Mar. 21, 2017.
Notice of Allowance and Fees Due for U.S. Appl. No. 14/429,280, "Micro-Fluidic Device and Uses Thereof", dated Jun. 26, 2017.
Supplementary European Search Report for EP Application No. 15752783.9, "Biophysically Sorted Osteoprogenitors From Culture Expanded Bone Marrow Derived Mesenchymal Stromal Cells (MSCs)", dated Jun. 30, 2017.
Notification of Transmittal of the International Search Report and the Written Opinion of the International Searching Authority, or the Declaration, International Search Report and Written Opinion for (56) References Cited

OTHER PUBLICATIONS

International Application No. PCT/US2015/050628, entitled: "System and Method for Inertial Focusing Microfiltration for Intra-Operative Blood Salvage Autotransfusion," dated Dec. 21, 2015.
Notification of Transmittal of the International Search Report and the Written Opinion of the International Searching Authority, or the Declaration, International Search Report and Written Opinion for International Application No. PCT/US2015/050604, entitled: "Microfluidic System and Method for Perfusion Bioreactor Cell Retention," dated Dec. 7, 2015.
Kim et al.; "Characterization of Different Subpopulations from Bone Marrow-Derived Mesenchymal Stromal Cells by Alkaline Phosphatase Expression," Stem Cells and Development (2012); vol. 21, No. 16; pp. 2958-2968.
Non-Final Office Action for U.S. Appl. No. 15/119,534, "Biophysically Sorted Osteoprogenitors From Culture Expanded Bone Marrow Derived Mesenchymal Stromal Cells (MSCs)" dated Aug. 23, 2017.
Notice of Allowance for U.S. Appl. No. 15/119,534, "Biophysically Sorted Osteoprogenitors From Culture Expanded Bone Marrow Derived Mesenchymal Stromal Cells (MSCs)" dated Mar. 1, 2018.
Notification of Transmittal of the International Search Report and the Written Opinion of the International Searching Authority, or the Declaration for International Application No. PCT/US2015/050628, "System and Method for Inertial Focusing Microfiltration for Intra-Operative Blood Salvage Autotransfusion", dated Dec. 21, 2015.
Ashworth, A., et al., "Cell salvage as part of a blood conservation strategy in anaesthesia", *British Journal of Anaesthesia*, 105: 401-416 (2010).
Esper, S.A., et al., "Intra-operative cell salvage: a fresh look at the indications and contraindications", *Blood Transfus*, 9: 139-47 (2011).
Munoz, M., et al., "Transfusion of post-operative shed blood: laboratory characteristics and clinical utility", *European Spine Journal*, 13 (Suppl. 1): S107-S113 (2004).
Madjdpour, C., et al., "Risks, benefits, alternatives and indications of allogenic blood transfusions", *Minerva Anestesiol*, 72: 283-98 (2006).
Madjdpour, C., et al., "Allogeneic red blood cell transfusions: efficacy, risks, alternatives and indications", *British Journal of Anaesthesia*, 95(1): 33-42 (2005).
Cross, MH., "Autotransfusion in cardiac surgery", Perfusion, 16: 391-400 (2001).
Edelman, M.J., et al., "The potential for reintroduction of tumor cells during intraoperative blood salvage: reduction of risk with use of the RC-400 leukocyte depletion filter", *Urology*, 47 (1996) 179-181.
Perseghin, P., et al., "Effectiveness of leukocyte filters in reducing tumor cell contamination after intraoperative blood salvage in lung cancer patients", *Vox sanguinis*, 72: 221-224 (1997).
Hou, H.W., et al., Isolation and retrieval of circulating tumor cells using centrifugal forces, Scientific Reports, 3: 1259, p. 1-8 (2013).
Bhagat, A.A.S., et al., "Continuous particle separation in spiral microchannels using dean flows and differential migration", *The Royal Society of Chemistry Lab on a Chip*, 8(11): 1906-1914 (2008).
Warkiani, M.E., et al., "Slanted spiral microfluidics for the ultra-fast, label-free isolation of circulating tumor cells", *The Royal Society of Chemistry Lab on a Chip*, 14: 128-137 (2014).
K.M. Skubitz, et al., CD66a, CD66b, CD66c, and CD66d each independently stimulate neutrophils, Journal of leukocyte biology, 60 (1996) 106-117.
T. Murakami, et al., Flow cytometric analysis of platelet activation markers CD62P and CD63 in patients with coronary artery disease, European journal of clinical investigation, 26 (1996) 996-1003.
Notification Concerning Transmittal of International Preliminary Report on Patentability for International Application No. PCT/US2015/050628, "System and Method for Inertial Focusing Microfiltration for Intra-Operative Blood Salvage Autotransfusion", dated Mar. 30, 2017.
Waters, J.H., "Intraoperative blood recovery", *ASAI O*: 1992, 59(1): 11-7 (2013).

\* cited by examiner

FIG. 7

SYSTEM AND METHOD FOR INERTIAL FOCUSING MICROFILTRATION FOR INTRA-OPERATIVE BLOOD SALVAGE AUTOTRANSFUSION

RELATED APPLICATION

This application is the U.S. National Stage of International Application No. PCT/US2015/050628, filed Sep. 17, 2015, which designates the U.S., published in English, and claims the benefit of U.S. Provisional Application No. 62/051,581, filed Sep. 17, 2014, The entire teachings of the above applications are incorporated herein by reference.

BACKGROUND OF THE INVENTION

Intra-operative blood loss is a dreaded complication in cancer surgery [1]. The average blood loss during bone cancer surgery is approximately 2 liters. This is presently replenished by allogeneic blood transfusion which places an enormous burden on blood banks, as well as exposes patients to risks related to blood transfusion namely infection, immunosuppression, tumour progression and transfusion reactions [2]. The alternative method for replenishing blood loss is 'intra-operative cell salvage' (IOCS) system where the blood lost during surgery can be salvaged and returned to the patient instead of discarding it [3]. However, IOCS has been avoided in tumour surgery because of theoretical concern of returning tumour cells to the patients.

Intra-operative blood loss results from tumour hypervascularity, tumour invasion of soft tissues, and large feeding blood vessels to the tumour [4]. Measures routinely employed by surgeons to minimize intra-operative blood loss include assessment and correction of coagulopathy; pre-operative tumour embolization. During the operation, control of blood can be achieved by the use of drugs like tranexamic acid, intra-operative ligation of feeding vessels, the use of bipolar electrocautery, and haemostatic agents like Gelfoam and thrombin (Floseal, Baxter).

Despite the above, patients undergoing cancer surgeries are still exposed to a significant intra-operative bleeding. This blood loss is presently replenished by allogeneic blood transfusion (ABT) at most centers all over the world. It has been shown that patients undergoing major cancer surgery are at increased risk of requiring massive transfusion (defined as requiring >10 units of packed red cell transfusion over a 24 hour period) than the average patient [5]. This places an enormous burden on the precious blood bank resources. At the same time, there is an increased awareness of the deleterious effects of ABT, especially in cancer surgery. These include post-operative infection, promotion of tumour growth, which is thought to occur secondary to immunosuppression, and other transfusion reactions. Moreover, ABT is associated with longer hospital stays, thereby leading to higher treatment costs. To combat this problem, there has been an emergence of alternatives such as auto-transfusion or intra-operative cell salvage (IOCS) system [6].

Using IOCS system, the blood lost during surgery can be salvaged and returned to the patient instead of discarding it. However, IOCS is contraindicated in cancer surgery since it was first introduced because of the theoretical concern of re-infusing tumour cells to the patients and then promoting tumour dissemination. However there has been no concrete evidence to support such statement in ensuing three decades [7]. On the contrary, there have been a number of studies supporting the effectiveness of IOCS especially when used in combination with Leukocyte Depletion Filter (LDF) in tumour surgery in different surgical specialties across hepatobiliary, gynaecology, gastrointestinal, urology and lung cancer surgery. Despite the evidence of efficacy of IOCS-LDF combination in a number of surgical oncology, there are drawbacks of using LDF filter for blood salvaged in surgical oncology [8]. The filtered blood, however, is rich in red blood cells but may be devoid of white blood cells and platelets. There would be a definite theoretical advantage in preserving white blood cells to provide the patient with immunogenic cells to fight against infection.

SUMMARY OF THE INVENTION

In accordance with an embodiment of the invention, there is provided a system for intra-operative blood salvage autotransfusion. The system comprises at least one inlet configured to receive whole blood of a patient; at least one curvilinear microchannel in fluid flow connection with the at least one inlet, the at least one curvilinear microchannel being adapted to isolate circulating tumor cells in the whole blood, based on cell size, along at least one portion of a cross-section of the at least one curvilinear microchannel; and at least two outlets in fluid flow connection with the at least one curvilinear microchannel, at least one outlet of the at least two outlets being configured to flow the circulating tumor cells isolated from the whole blood, and at least one other outlet of the at least two outlets being configured to flow at least a portion of a remainder of the whole blood, cleansed of the isolated circulating tumor cells, for return to the patient.

In further, related embodiments, the at least one curvilinear microchannel may comprise at least one spiral channel. The at least one curvilinear microchannel may comprise a plurality of curvilinear microchannels; the at least one inlet of each curvilinear microchannel of the plurality of curvilinear microchannels being in fluid flow connection with a common inlet of the system; and the at least two outlets of each curvilinear microchannel of the plurality of curvilinear microchannels being in fluid flow connection with at least two respective common outlets of the system. The system may comprise a plurality of channel layers attached to each other, each channel layer of the plurality of channel layers comprising at least some curvilinear microchannels of the plurality of curvilinear microchannels; the system further comprising a guide layer attached to the plurality of channel layers, the guide layer comprising the common inlet and the at least two common outlets for the plurality of curvilinear microchannels. The system may be configured to receive a continuous flow of whole blood at the at least one inlet, and to provide a continuous flow of isolated circulating tumor cells to the at least one outlet of the at least two outlets, and to provide a continuous flow of the at least a portion of the remainder of the whole blood for return to the patient.

In further related embodiments, the at least one curvilinear microchannel may be adapted to isolate the circulating tumor cells solely due to hydrodynamic forces in the at least one curvilinear microchannel, without use of a membrane in the microfluidic system. The at least one curvilinear microchannel may have a length, and the cross-section may have a height and a width defining an aspect ratio, such that the curvilinear microchannel is adapted, by virtue of the length and the cross-section, to isolate the circulating tumor cells in the whole blood along the portions of the cross-section of the channel based on the cell size. The cross-section of the at least one curvilinear microchannel may be a trapezoidal cross section defined by a radially inner side, a radially outer side, a bottom side, and a top side, the trapezoidal cross section having a) the radially inner side and the radially outer side unequal in height, or b) the radially inner side equal in height to the radially outer side, and wherein the top side has at least two continuous straight sections, each unequal in width to the bottom side. The cross-section of the at least one curvilinear microchannel may be a rectangular cross-section. The at least one curvilinear microchannel may be adapted to filter the whole blood by isolating the circulating tumor cells in the whole blood near one side of the at least one curvilinear microchannel, and to collect the at least a portion of the remainder of the whole blood on another side of the at least one curvilinear microchannel.

In further related embodiments, at least a portion of the remainder of the whole blood may comprise white blood cells, red blood cells and platelets at substantially the same concentrations as in the whole blood received at the at least one inlet. The at least a portion of the remainder of the whole blood may be substantially not depleted of white blood cells. At least about 95% of any circulating tumor cells in the whole blood received at the at least one inlet may be isolated as the isolated circulating tumor cells. The at least one inlet may be configured to receive the whole blood during surgery being performed on the patient; and/or to receive the whole blood after surgery having been performed on the patient.

Related method embodiments are provided.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

An embodiment according to the invention provides a passive multiplex inertial focusing microfiltration system to remove cancer cells from whole blood salvaged during cancer surgery. This novel microfiltration platform consists of multiple layer of PDMS sheets embossed with curvilinear microchannels (i.e., ~1-10000 spiral microchannels with trapezoidal or rectangular cross-section) bonded together for continual-based cell separation from large volume of blood. This approach exploits the differences in the size of the cells to separate the larger cancer cells from the predominantly smaller blood cells.

In accordance with an embodiment of the invention, there is provided a microfiltration system which can filter the tumour cells from blood salvaged during cancer surgery. The technique utilizes the inherent Dean vortex flows present in curvilinear microchannels under continuous flow, along with inertial lift forces which focus larger cancer cells against the outer wall (i.e., where strong vortices exist) while smaller hematologic cells (white blood cells (WBCs), red blood cells (RBCs) and platelets) remained unfocused in the entire channel and exist from both outlets. As the technique relies on high speed microfluidic dynamics, it is capable of achieving ultra-high throughput processing of one to two liters of blood under 30 min through a multiplexed approach of combining a number of these spiral microfluidics.

In accordance with an embodiment of the invention, a multiplexed inertial focusing microfiltration system can replace LDF or IOCS-LDF combination. This system can remove the tumour cells from the salvaged blood and make it safe to be returned to the patient. The technique utilises the inherent Dean vortex flows present in curvilinear microchannels with trapezoid/rectangular cross-section under continuous flow, along with inertial lift forces which focus and trap larger cancer cells against the outer wall where strong Dean vortex presents. Smaller hematologic components remained unfocused in the channels and can be recovered from the both outlets (See FIG. 1) [9, 10]. By re-circulating the blood through the channels a few times, the system can successfully remove most of the cancer cells while collecting the majority of vital blood components (WBCs, RBCs and platelets) to return to the patient. Such transfusion will reduce the chance of transfusing allogeneic blood to the patients and ABT associated risks. This may also indirectly address other ABT related problems such as increased length of hospital stay, resource consumption, and hospital charges.

Figure 1:
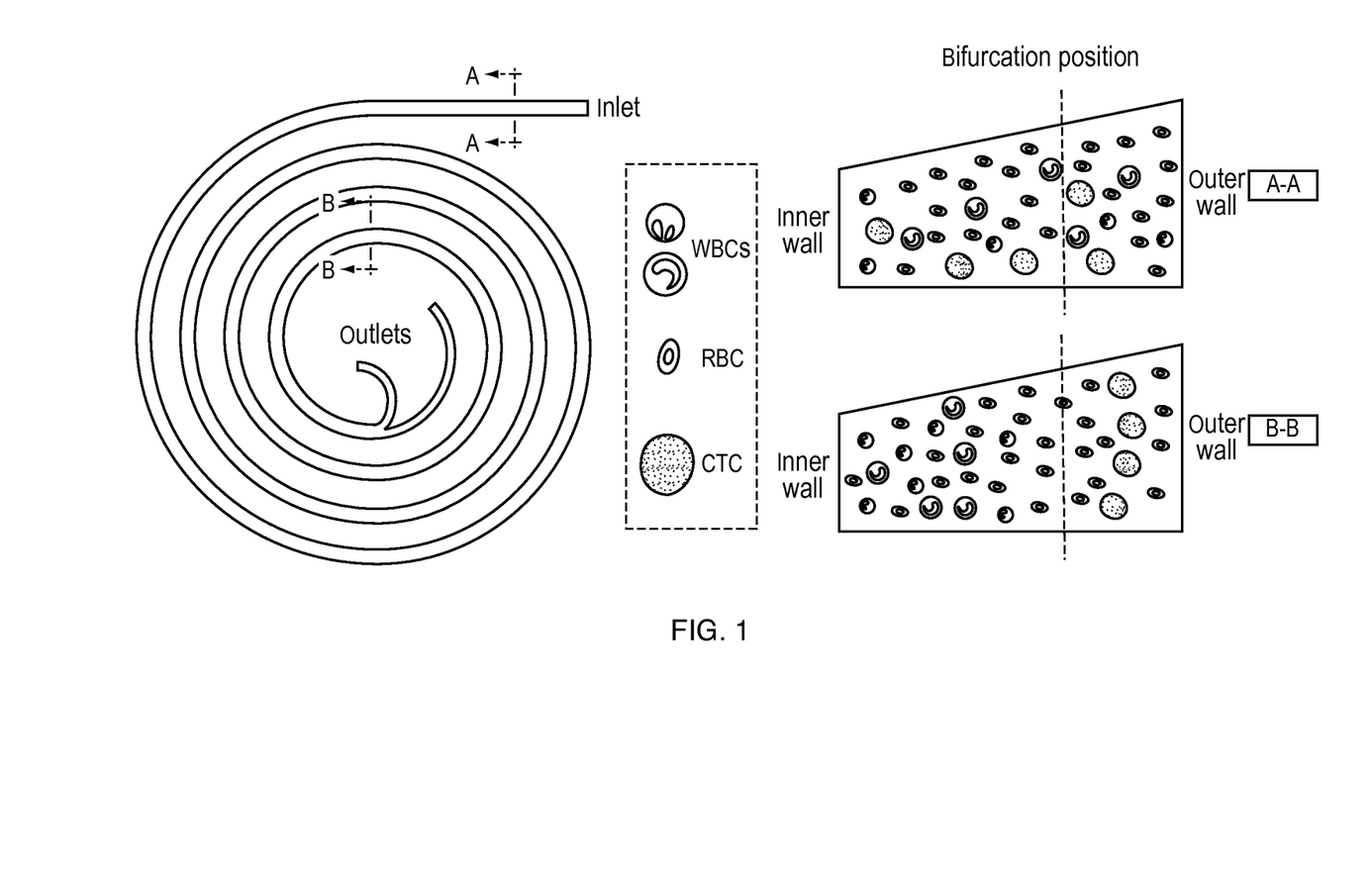
FIG. 1 is a schematic showing the top-view of a typical spiral micro-channel with trapezoidal cross-section (left), while the working principle of cancer cell separation from other blood components is depicted on the right side, in accordance with an embodiment of the invention.

FIG. 1 is a schematic showing the top-view of a typical spiral micro-channel with trapezoidal cross-section (left), in accordance with an embodiment of the invention. The working principle of cancer cells separation from other blood components is depicted on the right side. At the inlet (section A-A), whole blood enter the microchannels and then under the influence of inertial and Dean-drag forces, cancer cells which are typically larger than hematologic cells are trapped near the outer wall and exit from the outer outlet while smaller hematologic cells remain unfocused and exit from both outlets (section B-B). By repeating this procedure 3 times, majority of the blood cells (>90% RBCs, WBCs and platelets) can be recovered.

Figure 2A:
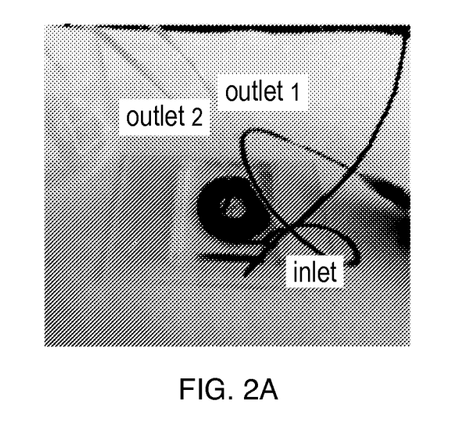
FIG. 2A is a photograph of a spiral microfluidic device with one inlet and two outlets, in accordance with an embodiment of the invention.
Figure 2B:
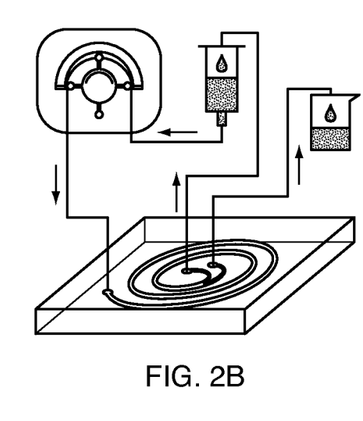
FIG. 2B is a schematic of the setup of a cyclic cell sorting system in accordance with an embodiment of the invention.
Figure 2C:
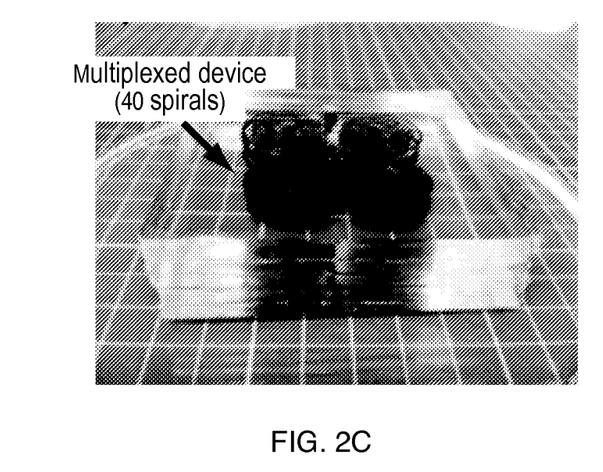
FIG. 2C is an optical image of a high-throughput system consisting of multiple layers of polymeric sheets with embossed microchannels (i.e., 40 spiral microchannels with trapezoidal cross-section) bonded together for continual blood purification from large sample volumes, in accordance with an embodiment of the invention.

Since processing of large volume of salvaged blood (i.e., 1-2 liters) requires utilizing a large number of spiral channels, an embodiment according to the invention provides an approach to combine many of these spiral shape channels together to achieve higher throughput. For this purpose, an integrated microfluidic platform consists of multiple layers of polymeric sheets with embossed microchannels (i.e., 4 spiral microchannels with trapezoidal cross-section in each layer) bonded together to make a multiplexed system with about 40 spirals (~200 ml/min). Theoretically, we can stack higher number of layers together to achieve even higher throughputs. However, for the concept of blood purification, we have just bonded 10 layers to achieve flow rate of around 200 ml/min facilitating process of 1 L of whole blood in just 5 min (see FIG. 2).

FIG. 2A is a photograph of a spiral microfluidic device with one inlet and two outlets, in accordance with an embodiment of the invention. The channels are filled with a red dye for visualization. The device is made of two PDMS layers bonded via plasma. One of the layers that have spiral pattern is casted from a micro-milling Aluminum mold. FIG. 2B is a schematic of the setup of a cyclic cell sorting system in accordance with an embodiment of the invention. Whole blood containing cancer cell can be pumped into microfluidic device using a peristaltic pump. Cancer cells will be separated from normal hematologic cells using hydrodynamic forces inside microchannels and clean blood can be returned to the patient after enrichment. FIG. 2C is an optical image of a high-throughput system consisting of multiple layers of polymeric sheets with embossed microchannels (i.e., 40 spiral microchannels with trapezoidal cross-section) bonded together for continual blood purification from large sample volumes, in accordance with an embodiment of the invention.

EXPERIMENTAL

In accordance with an embodiment of the invention, in order to find the optimum channel design that gives the maximum CTC removal and blood components return, spiral microchannels with various dimensions were fabricated using conventional micro-milling and soft lithography techniques [11].

Figure 3:
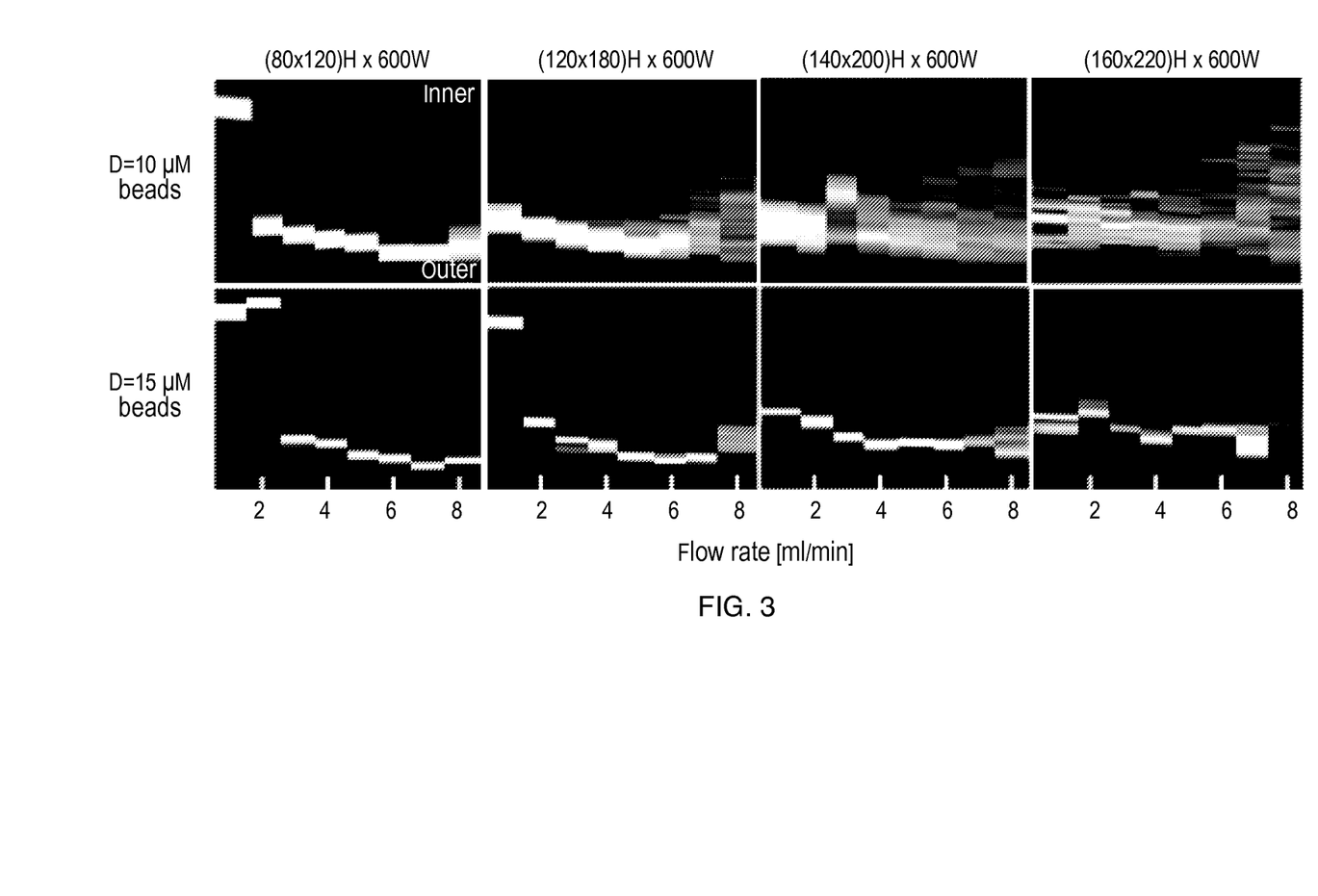
FIG. 3 is a top-view microscopy image demonstrating the focusing behaviour of fluorescent particles as a function of flow rate inside spiral channels with different trapezoid cross-sections and fixed width, in accordance with an embodiment of the invention.

FIG. 3 is a top-view microscopy image demonstrating the focusing behaviour of fluorescent particles as a function of flow rate inside spiral channels with different trapezoid cross-sections and fixed width, in accordance with an embodiment of the invention. Two different surrogates (10 and 15 µm beads) were used to mimic focusing position of WBCs and CTCs inside microchannels, respectively.

FIG. 3 presents fluorescent microscopy images demonstrating the focusing behavior of traceable particles (Nominal diameter of 15, 10 µm, Bangs Laboratories, Inc. USA) as a function of flow rate inside spiral channels. The aim was to focus 15 µm beads (resemble of cancer cells) near the outer wall while keeping the 10 µm beads (resemble of average hematologic cells) dispersed in the entire channel (see FIG. 4).

Figure 4:
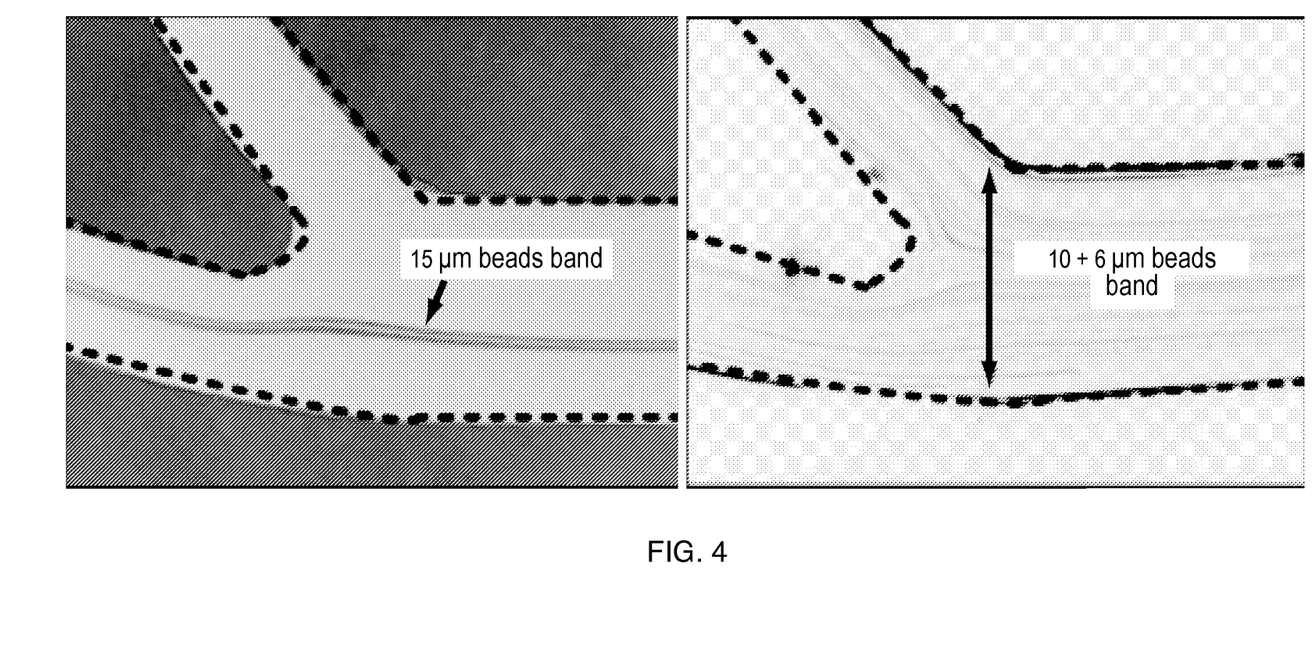
FIG. 4 shows fluorescent microscopy images of a device in accordance with an embodiment of the invention.

FIG. 4 shows fluorescent microscopy images of a device in accordance with an embodiment of the invention, showing the position of 15 and mixture of 10 & 6 µm beads spiked in the whole blood (~40% hr) near the device outlets at flow rate of 5 ml/min. The 15 µm beads (imitating cancer cells) are focused/trapped near the channel outer wall while 10 & 6 µm beads (imitating WBCs) remained unfocused exiting the device from both outlets. Yellow lines indicate the position of channel walls.

Figure 5A:
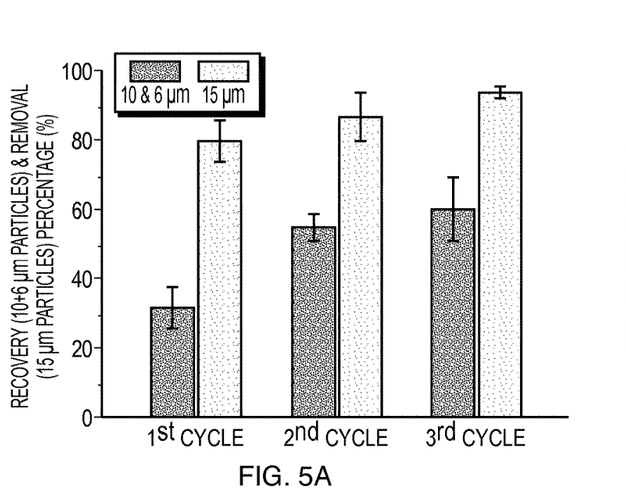
FIGS. 5A and 5B are a characterization of the high-throughput microfiltration system for blood purification, in accordance with an embodiment of the invention.
Figure 5B:
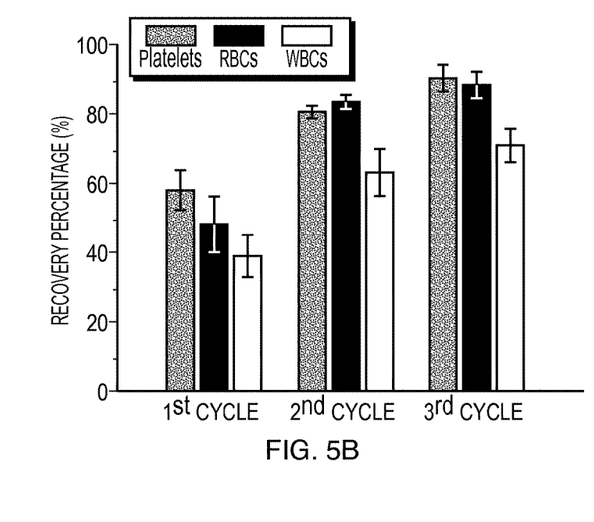

In accordance with an embodiment of the invention, the channel with trapezoid cross-section of 600 µm width and 140 µm (inner) and 180 µm (outer) depth and flow rate of 5 ml/min were chosen as an optimum design and parameter for blood purification. Our preliminary microfiltration tests using healthy blood samples (n=30 samples) revealed that this novel platform can return more than 90% of hematologic cells while removing the majority of deadly cancer cells (>92% efficiency) from blood thus making it safe to be returned to the patient body (see FIG. 5).

FIGS. 5A and 5B are a characterization of the high-throughput microfiltration system for blood purification, in accordance with an embodiment of the invention. FIG. 5A shows recovery and removal percentage of surrogate beads (10&6 µm and 15 µm) spiked in the whole blood after processing using the microfiltration system (3-cycle recirculation). FIG. 5B shows recovery percentage of hematologic cells (WBCs, RBCs and Platelets) from a spiral device with trapezoid cross-section. The amount of RBCs and Platelets were measured by a coulter counter, and the amounts of WBCs, were based on flow cytometry analysis of Hochest-positive, CD45-positive cells. Error bars indicate the standard deviation of results from three tests.

Figure 5C:
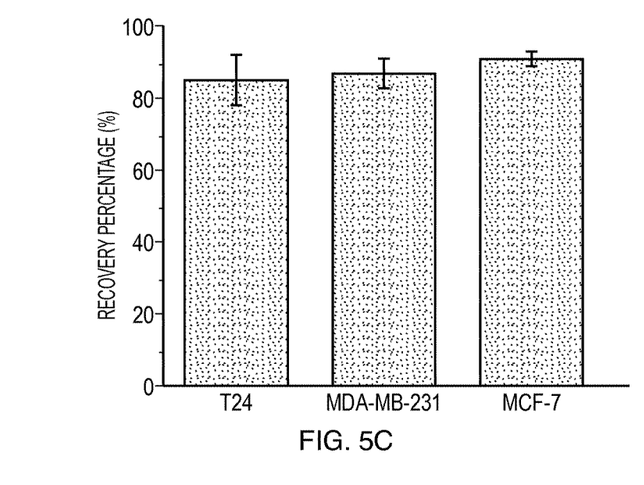
FIG. 5C shows removal percentages for T24, MDA-MB-231 and MCF-7, in accordance with an embodiment of the invention.

FIG. 5C shows removal percentages for T24, MDA-MB-231 and MCF-7, in accordance with an embodiment of the invention.

In addition, careful characterization of WBCs and platelets using standard markers (i.e., CD61, CD62P, CD66b and CD18) revealed no sign of activation due to processing using spiral device [12, 13]. Furthermore, we have not observed any hemolysis during the process confirming suitability of our technique for large-scale blood purification (see FIG. 6).

Figure 6A:
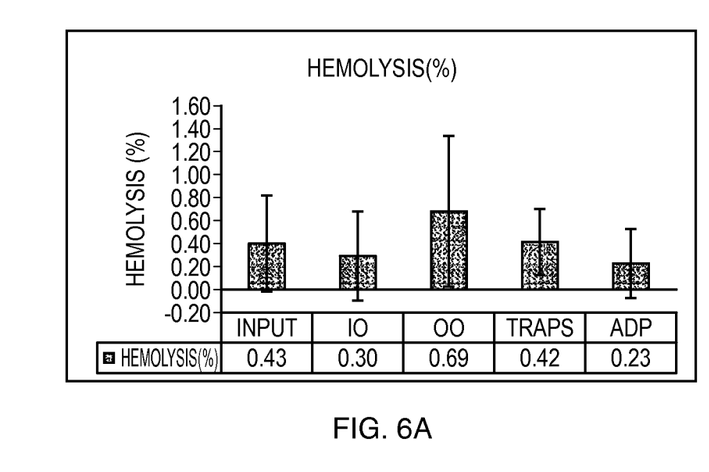
FIGS. 6A-6D show the effect of inertial forces on the blood components during separation using spiral device, in accordance with an embodiment of the invention.
Figure 6B:
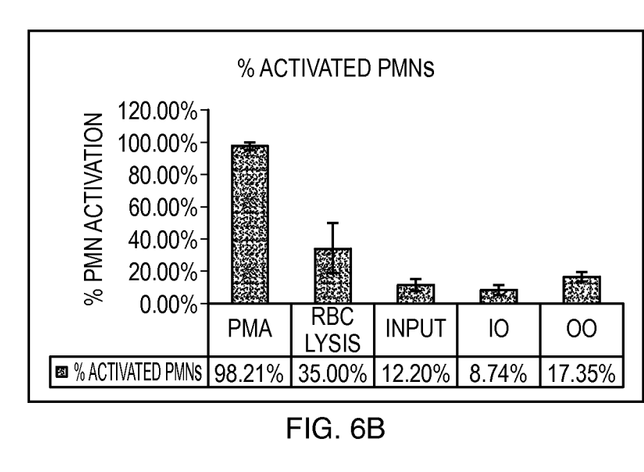
Figure 6C:
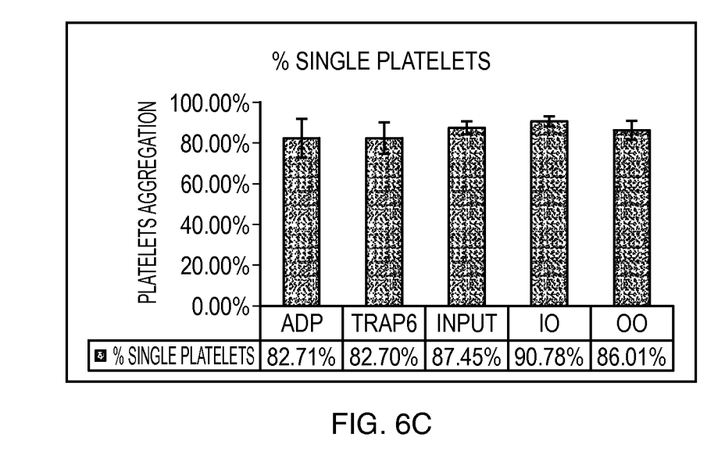
Figure 6D:
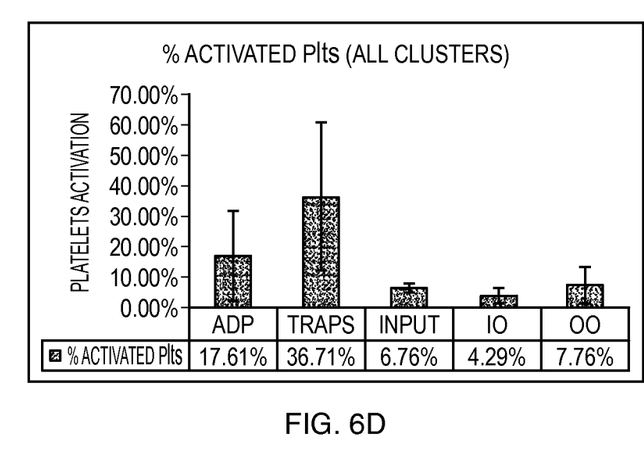

FIGS. 6A-6D show the effect of inertial forces on the blood components during separation using spiral device, in accordance with an embodiment of the invention. FIG. 6A shows the effect of spiral processing on the RBC lysis (hemolysis). It can be seen that spiral processing exerted no observable effect on hemolysis (IO: Inner Outlet, OO: Outer Outlet, TRAP6- or ADP-treated blood was the positive control for platelet activation). All the experiments were performed using NanoDrop on the plasma of collected samples. FIG. 6B shows that the effect of spiral processing on PMN (polymorphonuclear leukocytes) activation (i.e., using CD66b and CD18 antibodies) was less apparent as compared to that of RBC lysis method. (IO: Inner Outlet, OO: Outer Outlet, PMA-treated blood was the positive control for PMN activation). FIGS. 6C and 6D show the negligible effect of spiral processing on the Platelet's aggregation and activation, respectively. All the measurements were performed using standard protocols (i.e., using CD61 and CD62P antibodies) with appropriate controls.

Figure 7:
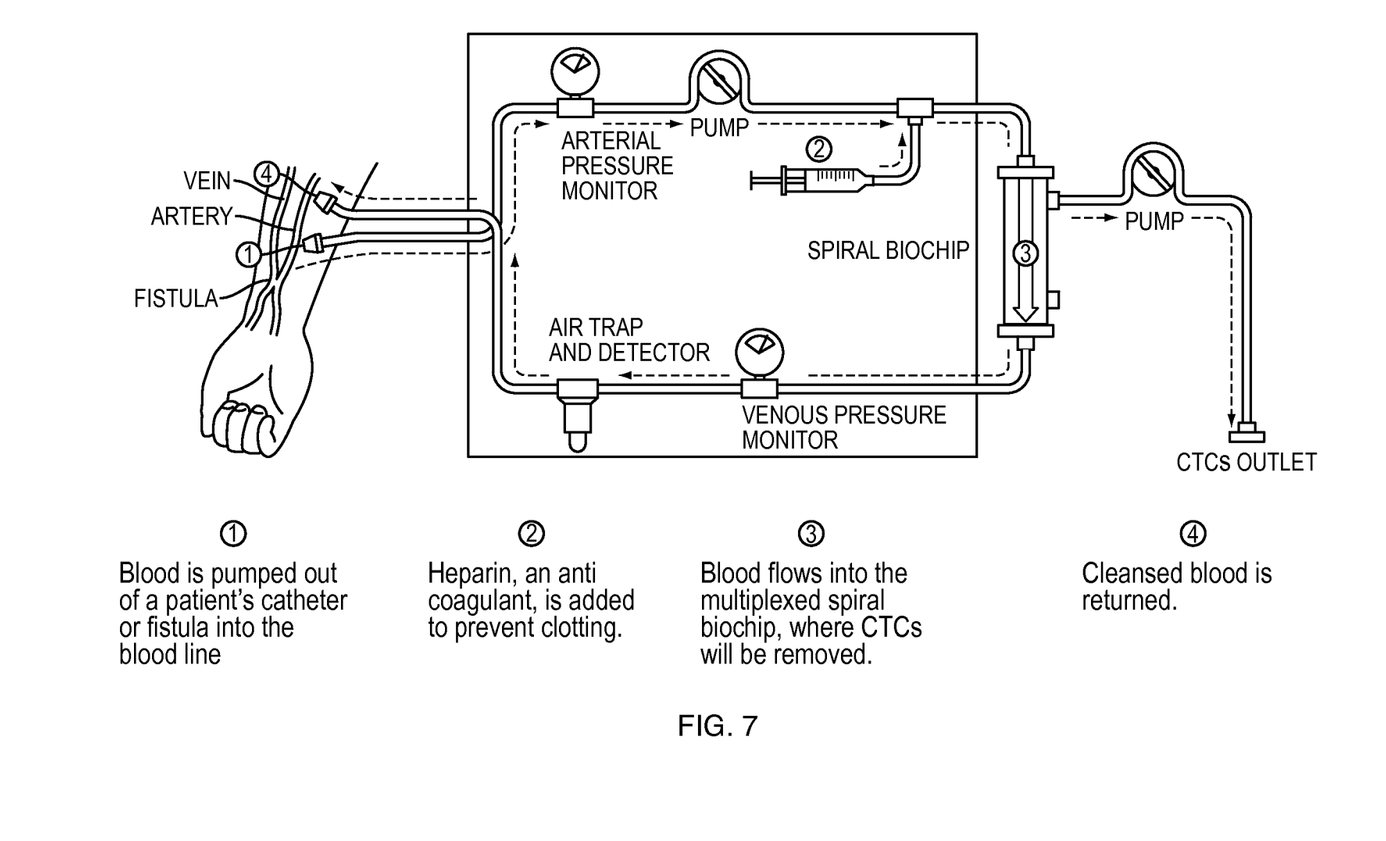
FIG. 7 is a schematic representation of the blood cleaning process using a multiplexed spiral biochip, in accordance with an embodiment of the invention.

FIG. 7 is a schematic representation of the blood cleaning process using a multiplexed spiral biochip, in accordance with an embodiment of the invention.

An embodiment according to the invention provides, a dedicated filtering system in the market which can safely remove and/or eradicate tumour cells from the salvaged blood with minimum damage to other blood components. This can be applied to all surgery involving cases where:

1—Significant blood loss can be expected—i.e. where the patient can benefit from IOCS use; and 2—Patient has malignant disease—i.e. where conventional IOCS is deemed contraindicated due to the potential danger of reinfusing tumour cells.

The filtration system offers a significant number of clinical benefits when utilised for intraoperative cell salvage, in accordance with an embodiment of the invention:

1—Reducing the chance of transfusing allogeneic blood to the patients and ABT associated risks.

2—Addressing other ABT related problems such as increased length of hospital stay, resource consumption, post-operative complications and hospital charges.

3—Reduction in donor demand.

Finally, the ultimate aim of the proposed multiplexed microfluidic system is to be a purifier for blood salvage during intraoperative cancer surgery or even can be used a direct purifier for cleaning of whole patient's blood after surgery and tumour resection in order to remove entire CTCs from blood stream and prevent cancer recurrence (see FIG. 7). We believe this new technology will be one of the essential components of the routine cancer surgery in the near future. In addition, this technique may be useful for blood preservation during transplantation, spinal surgery and neurosurgery.

The use of salvaged blood in tumour surgery has been tried and tested in a number of tumour surgeries, namely gynaecology, hepatobiliary, gastrointestinal and urology. However, return of salvaged blood has been avoided in tumour surgery because of theoretical concern of returning tumour cells to the patients. The approach in accordance with an embodiment of the invention is to introduce a newly developed filtering system which can filter the tumour cells from blood salvaged during cancer surgery. The main advantage of the system over existing microfilters is its ability to return all necessary blood components (WBCs, RBCs and Platelets) to the patient while removing almost all (>95%) the cancer cells. The method described here uses microfluidic dynamics to eliminate the Circulating tumor cells (CTCs) in real-time while exerting minimum damage to the normal hematologic cells. The CTCs are sorted via differences in physical properties as compared to other blood cells and thus eliminates the need of using expensive antibodies. The technique isolates and retrieves CTCs in a single step, thus decreasing the total processing time as well as costs. The simple design of spiral biochip with large channel dimensions prevent any clogging and facilitate multiplexing and automation. The simplicity in manufacturing (i.e., no pretreatment or antibody immobilization required) of the device and its ease of operation make it attractive for clinical applications requiring one-time use operation. Moreover, the device uses simple microfluidic channels, which can be produced at low-cost using conventional micro fabrication techniques.

A system in accordance with an embodiment of the invention can be used in, but is not limited to, applications including cells or particles separation (i.e., mammalian cell retention from bioreactors, yeast separation, blood fractionation, cancer cell removal) or enrichment, lab on a chip component for sample delivery and mixing and water filtration. This device has potential to be used for large-scale applications where filtration/fractionation of particles (ranging from 1-100 µm) from large volume of biological/clinical samples is required. In this novel microfiltration platform, separation is purely happening due to the hydrodynamic forces present in microchannels without any need for physical barriers or external field. Thus, it suits industrial applications, which need non-stop, continual filtration for a long period of time.

As used herein, a "curvilinear microchannel" is a microchannel in which a longitudinal axis along a direction of flow of the microchannel deviates from a straight line, and may, for example, be a spiral or sinusoidal channel.

As will be appreciated by those of ordinary skill in the art, the channel can have a variety of shapes (e.g., curved, spiral, multiloop, s-shaped, linear) provided that the dimensions of the channel are adapted to isolate cells in whole blood, based on cell size, along at least one portion of a cross-section of the at least one curvilinear microchannel.

In one aspect, the channel is curved. In a particular aspect the channel is a spiral. The height of the spiral channel can be in a range of between about 10 µm and about 200 µm, such as about 100 µm and about 140 µm. The width of the spiral channel can be in a range of between about 100 µm and about 500 µm. The length of the spiral channel can be in a range of between about 1 cm and about 10 cm.

In one aspect, the spiral channel can be a bi-loop spiral channel. In another aspect, the spiral channel can be 2-loop spiral channel. In yet another aspect, the spiral channel can be 3-loop spiral channel. In still another aspect, the spiral channel can be 4-loop spiral channel. In another aspect, the spiral channel can be 5-loop spiral channel, etc.

The radius of the spiral channel can be adapted to yield a Dean number in a range of between about 1 and about 10, such as a radius of about 1 cm that yields a Dean number equal to about 5. The length of the spiral channel can be equal to or greater than about 3 cm, such as about 9 cm, about 10 cm, about 15 cm, and about 20 cm. The width of the spiral channel can be in a range of between about 100 µm and about 1,000 µm, such as about 200 µm, about 300 µm, about 400 µm, about 500 µm, about 600 µm, about 700 µm, about 800 µm, and about 900 µm. The height of the spiral channel can be in a range of between about 20 µm and about 200 µm, such as about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, and about 190 µm. The aspect ratio of the channel can be in a range of between about 0.1 and about 1, such as about 0.12, about 0.2, about 0.3, about 0.4, about 0.5, about 0.6, about 0.7, about 0.8, and about 0.9.

As used herein, an "aspect ratio" is the ratio of a channel's height divided by its width and provides the appropriate cross section of the channel to isolate cells in whole blood, based on cell size, along at least one portion of a cross-section of the at least one curvilinear microchannel.

In accordance with an embodiment of the invention, microchannels, including spiral microchannels, may be used that are taught in U.S. Patent App. Pub. No. 2013/0130226 A1 of Lim et al., the entire disclosure of which is incorporated herein by reference. For example, among other things, teachings of flow rates, widths, heights, aspect ratios and lengths and other conditions relating to hydrodynamic isolation of cells may be used.

REFERENCES

[1] A. Ashworth, A. Klein, Cell salvage as part of a blood conservation strategy in anaesthesia, British Journal of Anaesthesia, 105 (2010) 401-416.
[2] J. H. Waters, Intraoperative blood recovery, ASAIO journal (American Society for Artificial Internal Organs: 1992), 59 (2013) 11.
[3] M. Munoz, J. Garcia-Vallejo, M. Ruiz, R. Romero, E. Olalla, C. Sebastian, Transfusion of post-operative shed blood: laboratory characteristics and clinical utility, European Spine Journal, 13 (2004) S107-S113.
[4] C. Madjdpour, V. Heindl, D. Spahn, Risks, benefits, alternatives and indications of allogenic blood transfusions, Minerva anestesiologica, 72 (2006) 283-298.
[5] C. Madjdpour, D. Spahn, Allogeneic red blood cell transfusions: efficacy, risks, alternatives and indications, British Journal of Anaesthesia, 95 (2005) 33-42.
[6] M. Cross, Autotransfusion in cardiac surgery, Perfusion, 16 (2001) 391-400.
[7] M. J. Edelman, P. Potter, K. G. Mahaffey, R. Frink, R. B. Leidich, The potential for reintroduction of tumor cells during intraoperative blood salvage: reduction of risk with use of the RC-400 leukocyte depletion filter, Urology, 47 (1996) 179-181.
[8] P. Perseghin, M. Vigano, G. Rocco, C. Pona, A. Buscemi, A. Rizzi, Effectiveness of leukocyte filters in reducing tumor cell contamination after intraoperative blood salvage in lung cancer patients, Vox sanguinis, 72 (1997) 221-224.
[9] W. M. Hou H W, Khoo B L, Li Z R, Soo R A, Tan D S W, Lim W T, Han J Y, Bhagat A A S, Lim C T, Isolation and retrieval of circulating tumor cells using centrifugal forces, Scientific Reports, (2013, In press.).
[10] A. A. S. Bhagat, S. S. Kuntaegowdanahalli, I. Papautsky, Continuous particle separation in spiral microchannels using dean flows and differential migration, Lab on a Chip, 8 (2008) 1906-1914.
[11] E. W. Majid, G. Guan, B. L. Khoo, W. C. Lee, A. A. S. Bhagat, D. S.-W. Tan, W. T. Lim, S. C. Lee, P. C. Chen, C. T. Lim, Slanted spiral microfluidics for the ultra-fast, label-free isolation of circulating tumor cells, Lab Chip, (2013).
[12] K. M. Skubitz, K. D. Campbell, A. Skubitz, CD66a, CD66b, CD66c, and CD66d each independently stimulate neutrophils, Journal of leukocyte biology, 60 (1996) 106-117.
[13] T. Murakami, Y. Komiyama, M. Masuda, H. Kido, S. Nomura, S. Fukuhara, M. Karakawa, T. Iwasaka, H. Takahashi, Flow cytometric analysis of platelet activation markers CD62P and CD63 in patients with coronary artery disease, European journal of clinical investigation, 26 (1996) 996-1003.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A system for intra-operative blood salvage autotransfusion, the system comprising:
at least one inlet configured to receive whole blood of a patient during a cancer surgery of the patient;
a plurality of curvilinear microchannels in fluid flow connection with the at least one inlet, the plurality of curvilinear microchannels being adapted to isolate circulating tumor cells in the whole blood, based on cell size, along at least one portion of a cross-section of such curvilinear microchannels;
at least two outlets in fluid flow connection with the plurality of curvilinear microchannels, at least one outlet of the at least two outlets being configured to flow the circulating tumor cells isolated from the whole blood, and at least one other outlet of the at least two outlets being configured to flow at least a portion of a remainder of the whole blood, cleansed of the isolated circulating tumor cells, to the patient as an autotransfusion;
the plurality of curvilinear microchannels flowing the whole blood at a flow rate, and the cross-section comprising a width and a height, such that the curvilinear microchannels are adapted to focus the circulating tumor cells near one wall of the curvilinear microchannels while also dispersing another component of the whole blood across a width of the curvilinear microchannels;
the plurality of curvilinear microchannels being multiplexed with each other to circulate the whole blood to be processed in a plurality of curvilinear microchannel cycles such that: (i) greater than 92% of the circulating tumor cells are directed to the at least one outlet that is configured to flow the circulating tumor cells isolated from the whole blood; and (ii) greater than 90% of each of: a red blood cell component of the whole blood, a white blood cell component of the whole blood, and a platelets component of the whole blood, are directed to the at least one other outlet that is configured to flow the at least a portion of the remainder of the whole blood to the patient as an autotransfusion.

2. The system of claim 1, wherein the plurality of curvilinear microchannels comprise a plurality of spiral channels.

3. The system of claim 1, wherein the system comprises a plurality of channel layers attached to each other, each channel layer of the plurality of channel layers comprising at least some curvilinear microchannels of the plurality of curvilinear microchannels;
the system further comprising a guide layer attached to the plurality of channel layers, the guide layer comprising a common inlet and at least two common outlets for the plurality of curvilinear microchannels.

4. The system of claim 1, configured to receive a continuous flow of whole blood at the at least one inlet,
and to provide a continuous flow of isolated circulating tumor cells to the at least one outlet of the at least two outlets,
and to provide a continuous flow of the at least a portion of the remainder of the whole blood for return to the patient.

5. The system of claim 1, wherein the plurality of curvilinear microchannels is adapted to isolate the circulating tumor cells solely due to hydrodynamic forces in the plurality of curvilinear microchannels, without use of a membrane in the microfluidic system.

6. The system of claim 1, wherein the curvilinear microchannels of the plurality of curvilinear microchannels have a length, and the cross-section has a height and a width defining an aspect ratio, such that the curvilinear microchannels are adapted, by virtue of the length and the cross-section, to isolate the circulating tumor cells in the whole blood along the portions of the cross-section of such channels based on the cell size.

7. The system of claim 1, wherein the cross-section of the curvilinear microchannels of the plurality of curvilinear microchannels is a trapezoidal cross section defined by a radially inner side, a radially outer side, a bottom side, and a top side, the trapezoidal cross section having a) the radially inner side and the radially outer side unequal in height, or b) the radially inner side equal in height to the radially outer side, and wherein the top side has at least two continuous straight sections, each unequal in width to the bottom side.

8. The system of claim 1, wherein the cross-section of the curvilinear microchannels of the plurality of curvilinear microchannels is a rectangular cross-section.

9. The system of claim 1, wherein the curvilinear microchannels of the plurality of curvilinear microchannels are adapted to filter the whole blood by isolating the circulating tumor cells in the whole blood near one side of the curvilinear microchannels, and to collect the at least a portion of the remainder of the whole blood on another side of the curvilinear microchannels.

10. The system of claim 1, wherein the at least a portion of the remainder of the whole blood comprises white blood cells, red blood cells and platelets at substantially the same concentrations as in the whole blood received at the at least one inlet.

11. The system of claim 1, wherein the at least a portion of the remainder of the whole blood is substantially not depleted of white blood cells.

12. The system of claim 1, wherein at least about 95% of any circulating tumor cells in the whole blood received at the at least one inlet are isolated as the isolated circulating tumor cells.

13. The system of claim 1, wherein the plurality of curvilinear microchannels are multiplexed with each other to flow at least about 200 milliliters per minute of the whole blood from the at least one other outlet to the patient as the autotransfusion.

14. A method for intra-operative blood salvage autotransfusion, the method comprising:
receiving whole blood of a patient during a cancer surgery of the patient and flowing the whole blood of the patient through at least one inlet of a system for intra-operative blood salvage autotransfusion;
flowing the whole blood from the at least one inlet through a plurality of curvilinear microchannels of the system in fluid flow connection with the at least one inlet, thereby isolating circulating tumor cells in the whole blood, based on cell size, along at least one portion of a cross-section of such curvilinear microchannels;
flowing the isolated circulating tumor cells through at least one outlet of at least two outlets of the system that are in fluid flow connection with the plurality of curvilinear microchannels, and flowing at least a portion of a remainder of the whole blood, cleansed of the isolated circulating tumor cells, through at least one other outlet of the at least two outlets of the system, to the patient as an autotransfusion;
the flowing the whole blood through the plurality of curvilinear microchannels comprising flowing the whole blood at a flow rate, and the cross-section comprising a width and a height, such that the circulating tumor cells are focused near one wall of the curvilinear microchannels while another component of the whole blood is dispersed across a width of the curvilinear microchannels;
the flowing of the whole blood comprising circulating the whole blood in a plurality of curvilinear microchannel cycles, such that: (i) greater than 92% of the circulating tumor cells are directed to the at least one outlet that flows the circulating tumor cells isolated from the whole blood; and (ii) greater than 90% of each of: a red blood cell component of the whole blood, a white blood cell component of the whole blood, and a platelets component of the whole blood, are directed to the at least one other outlet to the patient as an autotransfusion.

15. The method of claim 14, wherein the plurality of curvilinear microchannels comprise a plurality of spiral channels.

16. The method of claim 14, wherein the system comprises a plurality of channel layers attached to each other, each channel layer of the plurality of channel layers comprising at least some curvilinear microchannels of the plurality of curvilinear microchannels;
the system further comprising a guide layer attached to the plurality of channel layers, the guide layer comprising a common inlet and at least two common outlets for the plurality of curvilinear microchannels.

17. The method of claim 14, comprising continuously flowing whole blood through the at least one inlet;
providing a continuous flow of isolated circulating tumor cells to the at least one other outlet of the at least two outlets;
and providing a continuous flow of the at least a portion of the remainder of the whole blood for return to the patient.

18. The method of claim 14, comprising isolating the circulating tumor cells in the plurality of curvilinear microchannels solely due to hydrodynamic forces in the plurality of curvilinear microchannels, without use of a membrane in the system.

19. The method of claim 14, wherein the curvilinear microchannels of the plurality of curvilinear microchannels have a length, and the cross-section has a height and a width defining an aspect ratio, such that the curvilinear microchannels are adapted, by virtue of the length and the cross-section, to isolate the circulating tumor cells in the whole blood along the portions of the cross-section of such channels based on the cell size.

20. The method of claim 14, wherein the cross-section of the curvilinear microchannels of the plurality of curvilinear microchannels is a trapezoidal cross section defined by a radially inner side, a radially outer side, a bottom side, and a top side, the trapezoidal cross section having a) the radially inner side and the radially outer side unequal in height, or b) the radially inner side equal in height to the radially outer side, and wherein the top side has at least two continuous straight sections, each unequal in width to the bottom side.

21. The method of claim 14, comprising flowing at least about 200 milliliters per minute of the whole blood through the at least one other outlet to the patient as the autotransfusion.

* * * * *